US011624073B2

(12) United States Patent
Marchetti et al.

(10) Patent No.: US 11,624,073 B2
(45) Date of Patent: Apr. 11, 2023

(54) EXPRESSION VECTOR AND METHOD FOR THE STABLE PRODUCTION OF A PROTEIN IN A PLANT, IN PARTICULAR A WHOLE RECOMBINANT ANTIBODY IN A CEREAL ENDOSPERM

(71) Applicant: TRANSACTIVA S.R.L., Udine (IT)

(72) Inventors: Stefano Marchetti, Pagnacco (IT); Tamara Patti, Buja (IT)

(73) Assignee: TRANSACTIVA S.R.L., Udine (IT)

( * ) Notice: Subject to any disclaimer, the term of this patent is extended or adjusted under 35 U.S.C. 154(b) by 148 days.

(21) Appl. No.: 16/605,118

(22) PCT Filed: Apr. 16, 2018

(86) PCT No.: PCT/IT2018/050065
§ 371 (c)(1),
(2) Date: Oct. 14, 2019

(87) PCT Pub. No.: WO2018/189764
PCT Pub. Date: Oct. 18, 2018

(65) Prior Publication Data
US 2021/0214739 A1    Jul. 15, 2021

(30) Foreign Application Priority Data
Apr. 14, 2017    (IT) .................. 102017000042052

(51) Int. Cl.
    *C12N 15/82*    (2006.01)
    *C07K 16/28*    (2006.01)
(52) U.S. Cl.
    CPC ...... *C12N 15/8258* (2013.01); *C07K 16/2887* (2013.01); *C12N 15/8216* (2013.01)
(58) Field of Classification Search
    None
    See application file for complete search history.

(56) References Cited

U.S. PATENT DOCUMENTS

| 7,319,139 B2 * | 1/2008 | Braslawsky | ........... C12N 15/85 |
| | | | 530/387.3 |
| 2011/0038971 A1 * | 2/2011 | Marchetti | ............ C12N 9/2402 |
| | | | 424/776 |

FOREIGN PATENT DOCUMENTS

| WO | 2008/080954 A1 | 7/2008 |
| WO | 2009/112508 A1 | 9/2009 |
| WO | 2014/111858 A1 | 7/2014 |

OTHER PUBLICATIONS

Ko (Monoclon Antib Immunodiagn Immunother., 2014, 33(3): 192-198) (Year: 2014).*
Diamos et al (Front. Plant Sci., 2016, 7(200): 1-15) (Year: 2016).*
AIFA Position Paper with English Summary—May 13, 2013 (16 pages).
Conrad, Udo et al.: Expression of engineered antibodies in plant cells. Pant Molecular Biology 26: 1023-1030, 1994.
Datta, Karabi et al.: Indica Rice (*Oryza sative*, BR29 and IR64). Methods in Molecular Biology, vol. 343: Agrobacterium Protocols, 2.e, vol. 1, pp. 201-212.
De Buck, Sylvie et al.: Transgene silencing of invertedly repeated transgenes is released upon deletion of one of the transgenes involved. Pnat Molecular Biology 46: 433-445, 2001.
During, Klaus et al.: Synthesis and self-assembly of a functional monoclonal antibody in transgenic Nicotiana tabacum. Plant Molecular Biology 15: 281-293, 1990.
EMEA Guideline: Guideline on the Quality of Biological Active Substances Produced By Stable Transgene Expressionin Higher Plants. European Medicines Agency, Evaluation of Medicines for Human Use, pp. 1-11, Jul. 24, 2008.
Fojtova, Miloslava et al.: The trans-silencing capacity of invertedly repeated transgenes depends on their epigenetic state in tobacco. Nucleic Acids Research, vol. 34, No. 8, pp. 2280-2293, 2006.
Gallie, Daniel. et al.: Identification of the motifs within the tobacco mosaic virus 5'-leader responsible for enhancing translation. Nucleic Acids Research, vol. 20, No. 17, pp. 4631-4638, 1992.
Giddings, Glynis: Transgenic plants as protein factories. Institute of Biological Sciences, Current Opinion in Biotechnology, 12:450-454, 2001.
Hiatt, Andrew et al.: Production of antibodies in transgenic plants. Department of Molecular Biology, The Research Institute of Scripps Clinic, Nature, vol. 342, pp. 76-78, Nov. 2, 1989.
Hiei, Yukoh et al.: Efficient transformation of rice (*Oryza sativa* L.) mediated by Agrobacterium and sequence analysis of the boundaries of the T-DNA. The Plant Journal, 6 (20, pp. 271-282, 1994.
Lechtenberg, Berthold et al.: Neither inverted repeat T-DNA configurations nor arrangements of tandemly repeated transgenes are sufficient to trigger transgene sliencing. The Plant Journal 34, pp. 507-517, 2003.
Ma, Chonglie et al.: Intrinsic direct repeats generate consistent post-transcriptional gene silencing in tobacco. The Plant Journal 31(1) pp. 37-49, 2002.
Ma, Juliam K-C et al.: Characterization of a recombinant plant monoclonal secretory antibody and preventive immunotherapy in humans. Nature Medicine, vol. 4, No. 5, May 1998.
Ma, Juliam K-C et al.: The Production of Recombinant Pharmaceutical Proteins in Plants. Reviews, vol. 4, pp. 794-805, Oct. 2003.
Martinez de Alba, Angel Emilio et al.: Gene silencing in plants: A diversity of pathways. Biochimica et Biophysica Acta, 1829, pp. 1300-1308, 2013.
Meyer, P.: Homology-Dependent Gene Silencing in Plants. Annu. Rev. Plant Physiol. Plant Mol. Biol. 47, pp. 23-48, 1996.

(Continued)

*Primary Examiner* — Cathy Kingdom Worley
(74) *Attorney, Agent, or Firm* — Calfee, Halter & Griswold LLP

(57) ABSTRACT

Expression vector for the stable production of a protein in plants, in particular a whole recombinant antibody in a cereal endosperm, comprising an expression cassette for the light polypeptide chain (L) of the antibody and an expression cassette for the heavy polypeptide chain (H) of the antibody, having the same orientation and the same control and regulatory elements of gene expression.

15 Claims, 14 Drawing Sheets

Specification includes a Sequence Listing.

(56) References Cited

OTHER PUBLICATIONS

Mlotshwa, Sizolwenkosi et al.: Transcriptional Silencing Induced by *Arabidopsis* T-DNA Mutatns in Associated with 35S Promoter siRNAs and Requires Genes Involved in siRNA-dedicated Chromatin Silencing. Plant J. 64(4), pp. 699-704, Nov. 2010.
Muskens Marielle W.M. et al.: Role of inverted DNA repeats in transcriptional and post-transcriptional gene silencing. Plant Molecular Biology 43, pp. 243-260, 2000.
Obembe, Olawole O. et al.: Advances inplant molecular farming. Biotechnology Advances 29, pp. 210-222, 2011.
Otagaki, Shungo et al.: Size and positional effects of promoter RNA sedments on virus-induced RNA-directed DNA methylation and transcriptional gene silencing Epigenetics 6:6 pp. 681-691, Jun. 2011.
Ramessar, Koreen et al.: Cost-effective production of a vaginal protein microbicide to prevent HIV transmission. PNAS vol. 105, No. 10, pp. 3727-3732, Mar. 11, 2008.
Ramkumar, Thakku R. et al.: Effect of orientation of transcription of a gene in an inverted transferred DNA repeat on transcriptional gene silencing in rice transgenics-a case study. Physiol Mol Biol Plants 21(1), pp. 151-157, Jan.-Mar. 2015.
Rangan, L. et al.: Analysis of context Sequence Surrounding Translation Initiation Site from complete Genome of Model Plants. Mol Biotechnol 39, pp. 207-213, 2008.
Skarn, Magne et al.: An inverted repeat transgene with a structure that cannot generate double-stranded RNA, suffers silencing independent of DNA methylation. Transgenic Res 15, pp. 489-500, 2006.
Stam, Maike et al.: Distinct features of post-trancriptional gene silencing by antisense transgenes in single copy and inverted T-DNA repeat loci The Plant Journal 21(1), pp. 27-42, 2000.
Stoger, E. et al.: Recent Progress in Plantibody Technology. Current Pharmaceutical Design, 11, pp. 2439-2457, 2005.
Stoger, Eva et al.: Plant Molecular Pharming for the Treatment of Chronic and Infectious Diseases. Annu. Rev. Plant Biol. 65, pp. 743-768, 2014.
Vamvaka, Evangelia et al.: Rice endosperm produces an underglycosylated and potent form of the HIV-neutralizing monoclonal antibody 2G12. Plant Biotechnology Journal 14, pp. 97-108, 2016.
Villani, Maria Elena et al.: Plant pharming of full-sized, tumor-targeting antibody using different expression strategies. Plant Biotechnology Journal 7, pp. 59-72, 2009.
Wang, Ming-Co et al.: High-efficiency silencing of a β-glucuronidase gene in rice is correlated with repetitive transgene structure but is independent of DNA methylation. Plant Molecular Biology 43, pp. 67-82, 2000.
Ye, Fei et al.: RIGS(repeat-induced gene silencing) in *Arabidopsis* is transcriptional and alters chromatin configuration. Proc. Natl. Acad. Sci. USA, vol. 93, pp. 10881-10886, Oct. 1996.
International Search Report and Written Opinion from PCT/IT2018/050065 dated Jul. 13, 2018 (11 pages).
De Muynck et al.: "Production of antibodies in plants: status after twenty years", Plant Biotechnology Journal, vol. 8, No. 5, Feb. 3, 2010 (Feb. 3, 2010). pp. 529-563, XP055038516.
Rademacher T et al: "Recombinant antibody 2G12 produced in maize endosperm efficiently neutralizes HIV-1 and contains predominantly single-GlcNAc N-glycans", Plant Biotechnology Jou, Blackwell Pub, GB, vol. 6, No. 2, Feb. 1, 2008 (Feb. 1, 2008), pp. 189-201, XP008090758.
Zhong Huang et al: "High-level rapid production of full-size monoclonal antibodies in plants by a single-vector DNA replicon system", Biotechnology and Bioengineering, vol. 106, No. 1, May 1, 2010 (May 1, 2010), pp. 9-17, XP055106021.
Torres et al: Native and Artificial Reticuloplasmins Co-Accumulate in Distinct Domains of the Endoplasmic Reticulum and in Post-Endoplasmic Reticulum Compartments 11 , Plant Physiology, vol. 127, No. 3, Nov. 1, 2001 (Nov. 11, 2001), pp. 1212-1223, XP055426977.
Hensel et al , Transgenic roduction of an Anti HIV Antibody in the Barley Endosperm11 , Plos One, vol. 10, No. 10, Oct. 13, 2015 (Oct. 13, 2015), p. e0140476, XP055375088.
Nicholson et al: 1 A recombinant multimeric immunoglobulin expressed in rice shows assembly-dependent subcellular localization in endosperm cells: Assembly-dependent protein localization in rice endosperm11 , Plant Biotechnology Journal, vol. 3, No. 1. Nov. 2, 2004 (Nov. 2, 2004), pp. 115-127, XP055426987.
Orza Ez et al.: 11 Manufacturing antibodies in the plant cell 11 , Biotechnology Journal, vol. 4, No. 12, Dec. 1, 2009 (Dec. 1, 2009), pp. 1712-1724, XP055426986.

\* cited by examiner

A.
MATIAFSRLSIYFCVLLLCHGSMAQIVLSQSPAILSASPGE
KVTMTCRASSSVSYIHWFQQKPGSSPKPWIYATSNLASGVP
VRFSGSGSGTSYSLTISRVEAEDAATYYCQQWTSNPPTFGQ
GTKLEIKRTVAAPSVFIFPPSDEQLKSGTASVVCLLNNFYP
REAKVQWKVDNALQSGNSQESVTEQDSKDSTYSLSSTLTLS
KADYEKHKVYACEVTHQGLSSPVTKSFNRGEC (SEQ ID NO: 8)

B.
MATIAFSRLSIYFCVLLLCHGSMAQVQLQQPGAELVKPGAS
VKMSCKASGYTFTSYNMHWVKQTPGRGLEWIGAIYPGNGDT
SYNQKFKGKATLTADKSSSTAYMQLSSLTSEDSAVYYCARS
TYYGGDWYFNVWGAGTTVTVSAASTKGPSVFPLAPSSKSTS
GGTAALGCLVKDYFPEPVTVSWNSGALTSGVHTFPAVLQSS
GLYSLSSVVTVPSSSLGTQTYICNVNHKPSNTKVDKKAEPK
SCDKTHTCPPCPAPELLGGPSVFLFPPKPKDTLMISRTPEV
TCVVVDVSHEDPEVKFNWYVDGVEVHNAKTKPREEQYNSTY
RVVSVLTVLHQDWLNGKEYKCKVSNKALPAPIEKTISKAKG
QPREPQVYTLPPSRDELTKNQVSLTCLVKGFYPSDIAVEWE
SNGQPENNYKTTPPVLDSDGSFFLYSKLTVDKSRWQQGNVF
SCSVMHEALHNHYTQKSLSLSPGK (SEQ ID NO: 9)

| MH+_(mi) | Glycoform (composition in monosaccharides) | Glycoform (structure) |
|---|---|---|
| 1075.7 | FucHexNAc2Hex3 | Truncated form consisting of the fucosylated pentasaccharide core (2 N-acetylglucosamine (HexNAc) residues plus 3 mannose (Hex)) residues |
| 1209.7 | FucHexNAc2Hex3Xyl | Truncated form consisting of the fucosylated pentasaccharide core plus a xylose residue |
| 1283.7 | FucHexNAc3Hex3 | Truncated form consisting of the fucosylated pentasaccharide core plus an N-acetylglucosamine (HexNAc) residue | fig. 10

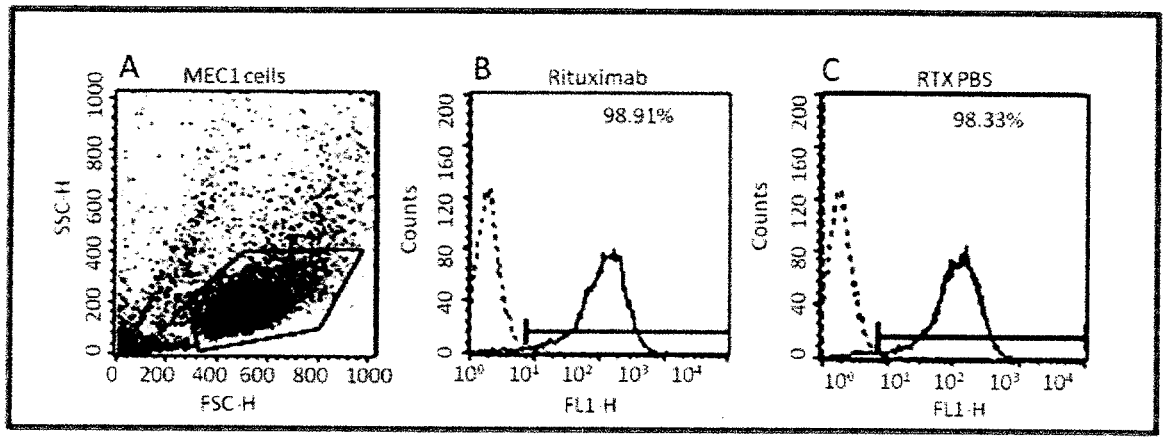

fig. 11a

| Sample | Mean fluorescence intensity |
|---|---|
| Rituximab | 138.38 |
| RTX PBS | 132.16 | fig. 11b

SEQUENCE LISTING

<160> NUMBER OF SEQ ID NOS: 9

<210> SEQ ID NO 1
<211> LENGTH: 15521
<212> TYPE: DNA
<213> ORGANISM: Artificial Sequence
<220> FEATURE:
<223> OTHER INFORMATION: Expression vector pTRS_Rituximab

<400> SEQUENCE: 1

| | | | | | |
|---|---|---|---|---|---|
| gaattcccga | tctagtaaca | tagatgacac | cgcgcgcgat | aatttatcct | agtttgcgcg | 60 |
| ctatattttg | ttttctatcg | cgtattaaat | gtataattgc | gggactctaa | tcataaaaac | 120 |
| ccatctcata | aataacgtca | tgcattacat | gttaattatt | acatgcttaa | cgtaattcaa | 180 |
| cagaaattat | atgataatca | tcgcaagacc | ggcaacagga | ttcaatctta | agaaacttta | 240 |
| ttgccaaatg | tttgaacgat | cggggaaatt | cgagctctca | gcactcgcca | cggttgaagg | 300 |
| acttggtcac | cgggctggac | aggccctggt | gggtcacctc | gcacgcatac | actttgtgct | 360 |
| tctcatagtc | ggctttggag | agcgtgaggg | tggaggacag | ggagtaggtg | gagtctttgg | 420 |
| agtcctgctc | ggtcacggac | tcctgggagt | tgccggactg | cagcgcattg | tcaactttcc | 480 |
| actgcacttt | ggcctcccga | gggtagaagt | tgttgagcag | gcacacaacg | gacgcggtgc | 540 |
| cggacttgag | ctgctcatcg | gagggaggga | agatgaacac | ggagggcgcg | gcaacggtcc | 600 |
| gcttgatctc | cagcttggtg | ccgccgccga | aggtgggagg | gttggaggtc | cactgctggc | 660 |
| agtagtaggt | ggcggcatcc | tcggcctcaa | cccgggagat | ggtgagggag | taggaggtgc | 720 |
| cggagccgga | gccggagaac | cgcaccggca | cgccggacgc | caggttggag | gtggcataga | 780 |
| tccagggctt | tgggctggag | cccggcttct | gctggaacca | atggatgtag | gacacggagg | 840 |
| aggacgcccg | gcaggtcatg | gtcactttct | cgcccgggct | cgcggacagg | atggccgggc | 900 |
| tctgggacag | cacaatctgg | gccatggagc | cgtggcacag | cagcagcacg | cagaagtaga | 960 |
| tggacagccg | ggagaacgca | atggtggcca | tggcttctag | aagctttgtt | gttgttgttg | 1020 |
| ttgttgttgt | tgttgttgtt | gttgttggaa | acttgatgtg | agttcaatga | cagggaagcc | 1080 |
| aacttatata | gtgaagaaaa | gaatcttcag | atatgacgta | gggatagagt | tgttgacat | 1140 |
| gtatagataa | tatctagcct | ataatgcgaa | aagtataata | gaaaaaaggt | agctttgcaa | 1200 |
| tgttgagata | tacacactat | gactcatgga | tgacatgtct | tgcgctttag | gggtaataca | 1260 |
| aacaatgctt | gttggtaaat | gtatatccaa | agccttaaga | tgttcctttg | ccttatggat | 1320 |
| aaatttcctt | ttgtgcaata | aagtttctct | agtatgttat | catttgtgc | ggtatgtcat | 1380 |
| agatgataag | ttaggcgctc | cttaaatttg | ttggtttgtt | gtcagttttg | cgtggcacac | 1440 |
| tatgcttgat | aagttagcgg | aacttttaaa | ataagaaact | tgtaagcttg | ttgtcatttt | 1500 |
| ctttgacata | ctatcctctc | ccatatgtaa | agtaaacaaa | ttgatgaaat | atatggaggt | 1560 |
| tagatgattt | tgcatatcca | actagtactt | ccaagtttat | accaaaaaat | agaaaatgtt | 1620 |
| ggatttaatt | tttaaaaaag | tagaagcaat | ggacttatgt | atctttttctt | ttttttatca | 1680 |
| ttatattttc | tggcgtgcat | ttattaggca | gtttattact | gtgacataaa | tttatttaac | 1740 |
| tcgccggtaa | taaatatgc | catatgtttg | ttagtcctca | ctgtcgacca | tatcatacaa | 1800 |
| gacattaatc | aaatcgtctt | gtctaaaatg | accacaatgt | ccctgcgtgg | tgtggactat | 1860 |
| gatttctttt | cattcatggt | tagaactact | gccggtccat | gaaaggttaa | actataaaat | 1920 |

```
gccatctgaa aaaaaaaagg taaacagaca agtactcgcc ctcgcaatta aattgttcaa    1980
taataataga aatggaagga tttgtcgtgt gtgtgtacat atatacaaga aaatatcagg    2040
aaagcatgta tgttatttta cacaccgaaa gaataaacgc acaacgaaac ttatatacaa    2100
tcatatgttt gctaggcaac cagagatgtt actcccaaaa gaaacgctcc ggtatcaatt    2160
caggcttctc ctctcacttg aactgcagct tgcttgcaaa tgtctggcca aacttccatc    2220
ctggtggcac gacgttggtg aagacgagcg tttggtcatc tgtgttggtg accctaaagg    2280
atagaccttg accggtgagg taggccagtg agtgccattg ggcgcccag ttacgtgcca     2340 tcggcatcca atccgctgtg ttggaaccca taacctccat ggacttgatt gaccctgccg    2400
ccgcgacgtt ggtcaccagt actagctgga agtagtcgtg accgttaatg gtgaaccgca    2460
ggccacccct cttcacgcaa ggaaccctgt agaattcgag ctcggtaccc ggggatcctc    2520
tagagtcgac ctgcaggcat gcaagcttgg cactggccgt cgttttacaa cgtcgtgact    2580
gggaaaaccc tggcgttacc caacttaatc gccttgcagc acatccccct ttcgccagct    2640
ggcgtaatag cgaagaggcc cgcaccgatc gcccttccca acagttgcgc agcctgaatg    2700
gcgaatgcta gagcagcttg agcttggatc agattgtcgt ttcccgcctt cagtttaaac    2760
ccgatctagt aacatagatg acaccgcgcg cgataattta tcctagtttg cgcgctatat    2820
tttgttttct atcgcgtatt aaatgtataa ttgcgggact ctaatcataa aaacccatct    2880
cataaataac gtcatgcatt acatgttaat tattacatgc ttaacgtaat tcaacagaaa    2940
ttatatgata atcatcgcaa gaccggcaac aggattcaat cttaagaaac tttattgcca    3000
aatgtttgaa cgatcgggga aattcgagct ctcacttgcc cgggctcagg gacagggact    3060
tctgggtgta atggttgtgc agcgcctcat gcatcacgga gcaggagaac acattgccct    3120
gctgccaccg ggacttgtca acggtgagct tggagtacag gaagaaggag ccatcggagt    3180
ccagcaccgg aggcgtggtc ttgtagttgt tctccggctg gccattggac tcccactcaa    3240
cggcaatgtc ggagggatag aagcctttca ccaggcaggt gagggacacc tggttcttgg    3300
tcagctcatc ccgggaggga ggcagggtgt acacctgagg ctcccgaggc tggcctttgg    3360
ctttggagat ggtcttctca atgggcgccg cagcgctttt gttggacact ttgcacttgt    3420 actcttttgcc attgagccag tcctggtgca gcacggtgag cacggacaca acccggtagg    3480
tggagttgta ctgctcctcc cgaggcttgg tcttggcatt gtgcacctcc acgccatcaa    3540
cataccagtt gaacttcacc tccgggtcct catgggacac atcaacaaca cgcaggtca    3600 cctccggcgt ccgggagatc atgagggtgt ctttgggctt gggagggaac aggaacacgg    3660
agggcccgcc cagcagctcc ggcgccgggc agggagggca ggtgtgggtc ttgtcgcagg    3720
acttgggctc ggctttcttg tcaactttgg tgttggaggg cttgtggttc acattgcaga    3780
tgtaggtctg ggtgcccagg gaggaggagg gcacggtcac aacggaggac agggagtaca    3840
ggccggagga ctgcagcacg gccgggaagg tgtgcacgcc ggaggtgagc gcgccggagt    3900
tccaggacac ggtcaccggc tccgggaagt agtctttcac caggcagccc agcgcggcg     3960 tgccgccgga ggtggacttg aggagggcg ccagagggaa cacggagggc cctttggtgg     4020
acgcggcgga cacggtcacg gtggtgccgg cgccccacac attgaagtac cagtcgccgc    4080
catagtaggt ggaccgcgcg cagtagtaca cggcggagtc ctcggaggtg agggaggaca    4140
gctgcatgta cgcggtggag gaggacttgt cggcggtgag ggtggctttg cctttgaact    4200
tctggttgta ggaggtgtcg ccattgcccg ggtagatggc gccaatccac tccaggccac    4260
ggcccggcgt ctgcttcacc caatgcatgt tgtaggaggt gaaggtgtag ccggacgctt    4320
```

```
tgcaggacat cttcacggac gcgcccggct tcaccagctc ggcgcccggc tgctgcagct    4380
gcacctgggc catggagccg tggcacagca gcagcacgca gaagtagatg gacagccggg    4440
agaacgcaat ggtggccatg gcttctagaa gctttgttgt tgttgttgtt gttgttgttg    4500
ttgttgttgt tgttggaaac ttgatgtgag ttcaatgaca gggaagccaa cttatatagt    4560
gaagaaaaga atcttcagat atgacgtagg gatagagttt gttgacatgt atagataata    4620
tctagcctat aatgcgaaaa gtataataga aaaaggtag ctttgcaatg ttgagatata     4680
cacactatga ctcatggatg acatgtcttg cgctttaggg gtaatacaaa caatgcttgt    4740
tggtaaatgt atatccaaag ccttaagatg ttcctttgcc ttatggataa atttcctttt    4800
gtgcaataaa gtttctctag tatgttatca ttttgtgcgg tatgtcatag atgataagtt    4860
aggcgctcct taaatttgtt ggtttgttgt cagttttgcg tggcacacta tgcttgataa    4920
gttagcggaa cttttaaaat aagaaacttg taagcttgtt gtcatttct ttgacatact     4980 atcctctccc atatgtaaag taaacaaatt gatgaaatat atggaggtta gatgattttg    5040
catatccaac tagtacttcc aagtttatac caaaaatag aaaatgttgg atttaatttt     5100
taaaaaagta gaagcaatgg acttatgtat cttttctttt ttttatcatt atattttctg    5160
gcgtgcattt attaggcagt ttattactgt gacataaatt tatttaactc gccggtaata    5220
aaatatgcca tatgtttgtt agtcctcact gtcgaccata tcatacaaga cattaatcaa    5280
atcgtcttgt ctaaaatgac cacaatgtcc ctgcgtggtg tggactatga tttcttttca    5340
ttcatggtta gaactactgc cggtccatga aaggttaaac tataaaatgc catctgaaaa    5400
aaaaaaggta aacagacaag tactcgccct cgcaattaaa ttgttcaata ataatagaaa    5460
tggaaggatt tgtcgtgtgt gtgtacatat atacaagaaa atatcaggaa agcatgtatg    5520
ttattttaca caccgaaaga ataaacgcac aacgaaactt atatacaatc atatgtttgc    5580
taggcaacca gagatgttac tcccaaaaga aacgctccgg tatcaattca ggcttctcct    5640
ctcacttgaa ctgcagcttg cttgcaaatg tctggccaaa cttccatcct ggtggcacga    5700
cgttggtgaa gacgagcgtt tggtcatctg tgttggtgac cctaaaggat agaccttgac    5760
cggtgaggta ggccagtgag tgccattggg cgccccagtt acgtgccatc ggcatccaat    5820
ccgctgtgtt ggaacccata acctccatgg acttgattga ccctgccgcc gcgacgttgg    5880
tcaccagtac tagctggaag tagtcgtgac cgttaatggt gaaccgcagg ccaccccttct   5940 tcacgcaagg aaccctgtag tttaaactat cagtgtttga caggatatat tggcgggtaa    6000
acctaagaga aaagagcgtt tattagaata acgatatttt aaaagggcgt gaaaaggttt    6060
atccgttcgt ccatttgtat gtgcatgcca accacagggt tcccctcggg atcaaagtac    6120
tttgatccaa cccctccgct gctatagtgc agtcggcttc tgacgttcag tgcagccgtc    6180
ttctgaaaac gacatgtcgc acaagtccta agttacgcga caggctgccg ccctgccctt    6240
ttcctggcgt tttcttgtcg cgtgttttag tcgcataaag tagaatactt gcgactagaa    6300
ccggagacat tacgccatga caagagcgc cgccgctggc ctgctgggct atgcccgcgt     6360
cagcaccgac gaccaggact tgaccaacca acgggccgaa ctgcacgcgg ccggctgcac    6420
caagctgttt tccgagaaga tcaccggcac caggcgcgac cgcccggagc tggccaggat    6480
gcttgaccac ctacgccctg gcgacgttgt gacagtgacc aggctagacc gcctggcccg    6540
cagcacccgc gacctactgg acattgccga gcgcatccag gaggccggcg cgggcctgcg    6600
tagcctggca gagccgtggg ccgacaccac cacgccggcc ggccgcatgg tgttgaccgt    6660
```

```
gttcgccggc attgccgagt tcgagcgttc cctaatcatc gaccgcaccc ggagcgggcg    6720
cgaggccgcc aaggcccgag gcgtgaagtt tggcccccgc cctaccctca ccccggcaca    6780
gatcgcgcac gcccgcgagc tgatcgacca ggaaggccgc accgtgaaag aggcggctgc    6840
actgcttggc gtgcatcgct cgaccctgta ccgcgcactt gagcgcagcg aggaagtgac    6900
gcccaccgag gccaggcggc gcggtgcctt ccgtgaggac gcattgaccg aggccgacgc    6960
cctggcggcc gccgagaatg aacgccaaga ggaacaagca tgaaaccgca ccaggacggc    7020
caggacgaac cgttttttcat taccgaagag atcgaggcgg agatgatcgc ggccgggtac    7080
gtgttcgagc gcccgcgca cgtctcaacc gtgcggctgc atgaaatcct ggccggtttg    7140
tctgatgcca agctggcggc ctggccggcc agcttggccg ctgaagaaac cgagcgccgc    7200
cgtctaaaaa ggtgatgtgt atttgagtaa acagcttgc gtcatgcggt cgctgcgtat    7260
atgatgcgat gagtaaataa acaaatacgc aaggggaacg catgaaggtt atcgctgtac    7320
ttaaccagaa aggcgggtca ggcaagacga ccatcgcaac ccatctagcc cgcgccctgc    7380
aactcgccgg ggccgatgtt ctgttagtcg attccgatcc ccagggcagt gcccgcgatt    7440
gggcggccgt gcgggaagat caaccgctaa ccgttgtcgg catcgaccgc ccgacgattg    7500
accgcgacgt gaaggccatc ggccggcgcg acttcgtagt gatcgacgga gcgccccagg    7560
cggcggactt ggctgtgtcc gcgatcaagg cagccgactt cgtgctgatt ccggtgcagc    7620
caagccctta cgacatatgg gccaccgccg acctggtgga gctggttaag cagcgcattg    7680
aggtcacgga tggaaggcta caagcggcct ttgtcgtgtc gcgggcgatc aaaggcacgc    7740
gcatcggcgg tgaggttgcc gaggcgctgg ccgggtacga gctgcccatt cttgagtccc    7800
gtatcacgca gcgcgtgagc tacccaggca ctgccgccgc cggcacaacc gttcttgaat    7860
cagaacccga gggcgacgct gcccgcgagg tccaggcgct ggccgctgaa attaaatcaa    7920
aactcatttg agttaatgag gtaaagagaa aatgagcaaa agcacaaaca cgctaagtgc    7980
cggccgtccg agcgcacgca gcagcaaggc tgcaacgttg gccagcctgg cagacacgcc    8040
agccatgaag cgggtcaact ttcagttgcc ggcggaggat cacaccaagc tgaagatgta    8100
cgcggtacgc caaggcaaga ccattaccga gctgctatct gaatacatcg cgcagctacc    8160
agagtaaatg agcaaatgaa taatgagta gatgaatttt agcggctaaa ggaggcggca    8220
tggaaaatca gaacaacca ggcaccgacg ccgtggaatg ccccatgtgt ggaggaacgg    8280
gcggttggcc aggcgtaagc ggctgggttg tctgccggcc ctgcaatggc actggaaccc    8340
ccaagcccga ggaatcggcg tgacggtcgc aaaccatccg gcccggtaca aatcggcgcg    8400
gcgctgggtg atgacctggt ggagaagttg aaggccgcgc aggccgccca gcggcaacgc    8460
atcgaggcag aagcacgccc cggtgaatcg tggcaagcgg ccgctgatcg aatccgcaaa    8520
gaatcccggc aaccgccggc agccggtgcg ccgtcgatta ggaagccgcc caagggcgac    8580
gagcaaccag attttttcgt tccgatgctc tatgacgtgg gcacccgcga tagtcgcagc    8640
atcatggacg tggccgtttt ccgtctgtcg aagcgtgacc gacgagctgg cgaggtgatc    8700
cgctacgagc ttccagacgg gcacgtagag gtttccgcag gccggccgg catggccagt    8760 gtgtgggatt acgacctggt actgatgcg gtttcccatc taaccgaatc catgaaccga    8820
taccgggaag ggaagggaga caagcccggc cgcgtgttcc gtccacacgt tgcggacgta    8880
ctcaagttct gccggcgagc cgatggcgga aagcagaaag acgacctggt agaaacctgc    8940
attcggttaa acaccacgca cgttgccatg cagcgtacga agaaggccaa gaacggccgc    9000
ctggtgacgg tatccgaggg tgaagccttg attagccgct acaagatcgt aaagagcgaa    9060
```

```
accgggcggc cggagtacat cgagatcgag ctagctgatt ggatgtaccg cgagatcaca    9120
gaaggcaaga acccggacgt gctgacggtt caccccgatt acttttttgat cgatcccggc   9180 atcggccgtt ttctctaccg cctggcacgc cgcgccgcag gcaaggcaga agccagatgg   9240
ttgttcaaga cgatctacga acgcagtggc agcgccggag agttcaagaa gttctgtttc   9300
accgtgcgca agctgatcgg gtcaaatgac ctgccggagt acgatttgaa ggaggaggcg   9360
gggcaggctg gcccgatcct agtcatgcgc taccgcaacc tgatcgaggg cgaagcatcc   9420
gccggttcct aatgtacgga gcagatgcta gggcaaattg ccctagcagg ggaaaaaggt   9480
cgaaaaggtc tctttcctgt ggatagcacg tacattggga acccaaagcc gtacattggg   9540
aaccggaacc cgtacattgg gaacccaaag ccgtacattg ggaaccggtc acacatgtaa   9600
gtgactgata taaagagaaa aaaggcgatt ttttccgcct aaaactcttt aaaacttatt   9660
aaaactctta aacccgcctg gcctgtgca taactgtctg gccagcgcac agccgaagag    9720
ctgcaaaaag cgcctaccct tcggtcgctg cgctccctac gccccgccgc ttcgcgtcgg   9780
cctatcgcgg ccgctggccg ctcaaaaatg gctggcctac ggccaggcaa tctaccaggg   9840
cgcggacaag ccgcgccgtc gccactcgac cgccggcgcc cacatcaagg caccctgcct   9900
cgcgcgtttc ggtgatgacg gtgaaaacct ctgacacatg cagctcccgg agacggtcac   9960
agcttgtctg taagcggatg ccgggagcag acaagcccgt cagggcgcgt cagcgggtgt   10020
tggcgggtgt cggggcgcag ccatgaccca gtcacgtagc gatagcggag tgtatactgg   10080
cttaactatg cggcatcaga gcagattgta ctgagagtgc accatatgcg gtgtgaaata   10140
ccgcacagat gcgtaaggag aaaataccgc atcaggcgct cttccgcttc ctcgctcact   10200
gactcgctgc gctcggtcgt tcggctgcgg cgagcggtat cagctcactc aaaggcggta   10260
atacggttat ccacagaatc aggggataac gcaggaaaga acatgtgagc aaaaggccag   10320
caaaaggcca ggaaccgtaa aaaggccgcg ttgctggcgt ttttccatag gctccgcccc   10380
cctgacgagc atcacaaaaa tcgacgctca agtcagaggt ggcgaaaccc gacaggacta   10440
taaagatacc aggcgtttcc ccctggaagc tccctcgtgc gctctcctgt tccgaccctg   10500
ccgcttaccg gatacctgtc cgcctttctc ccttcgggaa gcgtggcgct ttctcatagc   10560
tcacgctgta ggtatctcag ttcggtgtag tcgttcgct ccaagctggg ctgtgtgcac    10620
gaaccccccg ttcagcccga ccgctgcgcc ttatccggta actatcgtct gagtccaacc   10680
ccggtaagac acgacttatc gccactggca gcagccactg gtaacaggat tagcagagcg   10740
aggtatgtag gcggtgctac agagttcttg aagtggtggc ctaactacgg ctacactaga   10800
aggacagtat ttggtatctg cgctctgctg aagccagtta ccttcggaaa aagagttggt   10860
agctcttgat ccggcaaaca aaccaccgct ggtagcggtg ttttttgt ttgcaagcag     10920 cagattacgc gcagaaaaaa aggatctcaa gaagatcctt tgatctttc tacggggtct    10980 gacgctcagt ggaacgaaaa ctcacgttaa gggattttgg tcatgcattc taggtatcag   11040
aagaactcgt caagaaggcg atagaaggcg atgcgctgcg aatcgggagc ggcgataccg   11100
taaagcacga ggaagcggtc agcccattcg ccgccaagct cttcagcaat atcacgggta   11160
gccaacgcta tgtcctgata gcggtccgcc acacccagcc ggccacagtc gatgaatcca   11220
gaaaagcggc cattttccac catgatattc ggcaagcagg catcgccatg ggtcacgacg   11280
agatcctcgc cgtcgggcat gcgcgccttg agcctggcga acagttcggc tggcgcgagc   11340
ccctgatgct cttcgtccag atcatcctga tcgacaagac cggcttccat ccgagtacgt   11400
```

```
gctcgctcga tgcgatgttt cgcttggtgg tcgaatgggc aggtagccgg atcaagcgta    11460
tgcagccgcc gcattgcatc agccatgatg gatactttct cggcaggagc aaggtgagat    11520
gacaggagat cctgccccgg cacttcgccc aatagcagcc agtcccttcc cgcttcagtg    11580
acaacgtcga gcacagctgc gcaaggaacg cccgtcgtgg ccagccacga tagccgcgct    11640
gcctcgtcct gcagttcatt cagggcaccg gacaggtcgg tcttgacaaa aagaaccggg    11700 cgccctgcg ctgacagccg gaacacggcg gcatcagagc agccgattgt ctgttgtgcc     11760
cagtcatagc cgaatagcct ctccacccaa gcggccggag aacctgcgtg caatccatct    11820
tgttcaatca tttattattt ccttcctctt ttcggtgatg ctgccaactt actgattttag   11880 tgtatgatgg tgttttttgag gtgctccagt ggcttctgtt tctatcagct gtccctcctg   11940
ttcagctact gacggggtgg tgcgtaacgg caaaagcacc gccggacatc agcgctatct    12000
ctgctctcac tgccgtaaaa catggcaact gcagttcact tacaccgctt ctcaacccgg    12060
tacgcaccag aaaatcattg atatggccat gaatggcgtt ggatgccggg caacagcccg    12120
cattatgggc gttggcctca acacgatttt acgtcactta aaaaactcag gccgcagtcg    12180
gtaacctcgc gcatacagcc gggcagtgac gtcatcgtct gcgcggaaat ggacgaacag    12240
tggggctatg tcgggctaa atcgcgccag cgctggctgt tttacgcgta tgacagtctc     12300
cggaagacgg ttgttgcgca cgtattcggt gaacgcacta tggcgacgct ggggcgtctt    12360
atgagcctgc tgtcaccctt tgacgtggtg atatggatga cggatggctg gccgctgtat    12420
gaatcccgcc tgaagggaaa gctgcacgta atcagcaagc gatatacgca gcgaattgag    12480
cggcataacc tgaatctgag gcagcacctg gcacggctgg gacggaagtc gctgtcgttc    12540
tcaaaatcgg tggagctgca tgacaaagtc atcgggcatt atctgaacat aaaacactat    12600
caataagttg gagtcattac ccctcttttc tacagtattt aaagataccc caagaagcta    12660
attataacaa gacgaactcc aattcactgt tccttgcatt ctaaaacctt aaataccaga    12720
aaacagcttt tcaaagttg ttttcaaagt tggcgtataa catagtatcg acggagccga     12780
ttttgaaacc gcggtgatca caggcagcaa cgctctgtca tcgttacaat caacatgcta    12840
ccctccgcga gatcatccgt gtttcaaacc cggcagctta gttgccgttc ttccgaatag    12900
catcggtaac atgagcaaag tctgccgcct tacaacggct ctcccgctga cgccgtcccg    12960
gactgatggg ctgcctgtat cgagtggtga ttttgtgccg agctgccggt cggggagctg    13020
ttggctggct ggtggcagga tatattgtgg tgtaaacaaa ttgacgctta gacaacttaa    13080
taacacattg cggacgtttt taatgtactg aattaacgcc gaattaattc gggggatctg    13140
gattttagta ctggattttg gttttaggaa ttagaaattt tattgataga agtatttttac  13200 aaatacaaat acatactaag ggtttcttat atgctcaaca catgagcgaa acccatatagg  13260 aaccctaatt cccttatctg ggaactactc acacattatt atggagaaac tcgagttaca   13320
gcttgttgta aacacgcgct aaacggccgt ggcctttgac agtcaccggt gattcgttgg    13380
cggcaataaa cgctgattca cccggtttaa gctgtaactg ctgagaacct ttccacaacg    13440
ttgcatcgcc ttcgacgcag aacaaaatgg cggcactctg ctggctaatg gtggtttctt    13500
tatcactaag gtcatgcagc gagaaggcaa aatcatccac tggaatcggg aagtccagtt    13560
ctgcaccttg tttcaccggc tgggtcaaca actggttagc cggtttggct tcgaatttca    13620
cattggcaac cagttccgga atatcaatgt atttaggcgt cagacccgca cgcagcacgt    13680
tatcggagtt tgccatcact tccagcgcca cgccttgcag gtaagcgtgc ggtgtttcag    13740
cgaacaggaa catcgcttcg ccagggttca atttcaccac attcagcaat agcggggaga    13800
```

-continued

```
acagaccgct gtcttccggg taaaattcag aaattaaacg aatcgtttgc cacggttcac    13860
cctgctggct atcgagggcc gattttaaaa tcgccagcgc gcgggatttt tcttcaccct    13920
gcatattcaa caggctggcg aacagttcgc ttaaacgttc ggcatcaggc tgttgtaaaa    13980
agtgagcaat cgccggatgt gcacctgcga ccggctggag tagggagaca atctcggaaa    14040
attcacgaaa cgcgttcatc gcaaggaaag gcgtcagcgc aaaaaccagc tccggcttgt    14100
ggttaggatc tttatagtta cgctcggcgg catccatcgg gatacctgcg gcattttctt    14160
tggcaaaacc gatttcagaa ttgtgtttgt ttggatgaac ctgaatggag agtggctgtg    14220
ctgcgcataa tactttgaac aggaaaggca gttcgccaaa gcgtttggca acggcctctc    14280
cgagcagagt cgatttatca ctctcaatca catcacgcag tgaaacgatg tctccggcgg    14340
cattctgcac tcgtgaactg cttttcggat gtgcgcccat ccacagctcg gccatcggct    14400
ggctggacgg attttccata ccataaagtt cagtcaacgc cgttttgctg ccccaggcat    14460
agttttgcac tgagttaatg agttttttgca tctcgagaga gatagatttg tagagagaga    14520
ctggtgattt cagcgtgtcc tctccaaatg aaatgaactt ccttatatag aggaaggtct    14580
tgcgaaggat agtgggattg tgcgtcatcc cttacgtcag tggagatatc acatcaatcc    14640
acttgctttg aagacgtggt tggaacgtct tcttttttcca cgatgctcct cgtgggtggg    14700
ggtccatctt tgggaccact gtcggcgagg gcatcttgaa cgatagcctt tcctttatcg    14760
caatgatggc atttgtaggt gccaccttcc ttttctactg tccttttgat gaagtgacag    14820
atagctgggc aatggaatcc gaggaggttt cccgatatta ccctttgttg aaaagtctca    14880
atagcccttt ggtcttctga gactgtatct ttgatattct tggagtagac gagagtgtcg    14940
tgctccacca tgttatcaca tcaatccact tgctttgaag acgtggttgg aacgtcttct    15000
ttttccacga tgctcctcgt gggtggggt ccatctttgg gaccactgtc ggcagaggca    15060
tcttgaacga tagcctttcc tttatcgcaa tgatggcatt tgtaggtgcc accttccttt    15120
tctactgtcc ttttgatgaa gtgacagata gctgggcaat ggaatccgag gaggtttccc    15180
gatattaccc tttgttgaaa agtctcaata gccctttggt cttctgagac tgtatctttg    15240
atattcttgg agtagacgag agtgtcgtgc tccaccatgt tggcaagctg ctctagccaa    15300
tacgcaaacc gcctctcccc gcgcgttggc cgattcatta atgcagctgg cacgacaggt    15360
ttcccgactg gaaagcgggc agtgagcgca acgcaattaa tgtgagttag ctcactcatt    15420
aggcacccca ggctttacac tttatgcttc cggctcgtat gttgtgtgga attgtgagcg    15480
gataacaatt tcacacagga aacagctatg accatgatta c                       15521
```

<210> SEQ ID NO 2
<211> LENGTH: 1430
<212> TYPE: DNA
<213> ORGANISM: Oryza sativa
<220> FEATURE:
<223> OTHER INFORMATION: GluB-4 promoter

<400> SEQUENCE: 2

```
tacagggttc cttgcgtgaa gaagggtggc ctgcggttca ccattaacgg tcacgactac       60
ttccagctag tactggtgac caacgtcgcg gcggcagggt caatcaagtc catggaggtt      120
atgggttcca acacagcgga ttggatgccg atggcacgta actgggcgc ccaatggcac      180 tcactggcct acctcaccgg tcaaggtcta tcctttaggg tcaccaacac agatgaccaa      240
acgctcgtct tcaccaacgt cgtgccacca ggatggaagt ttggccagac atttgcaagc      300
```

```
aagctgcagt tcaagtgaga ggagaagcct gaattgatac cggagcgttt cttttgggag    360
taacatctct ggttgcctag caaacatatg attgtatata agtttcgttg tgcgtttatt    420
ctttcggtgt gtaaaataac atacatgctt tcctgatatt ttcttgtata tatgtacaca    480
cacacgacaa atccttccat ttctattatt attgaacaat ttaattgcga gggcgagtac    540
ttgtctgttt acctttttt tttcagatgg cattttatag tttaaccttt catggaccgg     600
cagtagttct aaccatgaat gaaaagaaat catagtccac accacgcagg gacattgtgg    660
tcattttaga caagacgatt tgattaatgt cttgtatgat atggtcgaca gtgaggacta    720
acaaacatat ggcatatttt attaccggcg agttaaataa atttatgtca cagtaataaa    780
ctgcctaata aatgcacgcc agaaaatata atgataaaaa aagaaaaga tacataagtc      840 cattgcttct acttttttaa aaattaaatc caacattttc tattttttgg tataaacttg    900
gaagtactag ttggatatgc aaaatcatct aacctccata tatttcatca atttgtttac    960
tttacatatg ggagaggata gtatgtcaaa gaaaatgaca acaagcttac aagtttctta   1020
ttttaaaagt tccgctaact tatcaagcat agtgtgccac gcaaaactga caacaaacca   1080
acaaatttaa ggagcgccta acttatcatc tatgacatac cgcacaaaat gataacatac   1140
tagagaaact ttattgcaca aaaggaaatt tatccataag gcaaggaac atcttaaggc     1200 tttggatata catttaccaa caagcattgt ttgtattacc cctaaagcgc aagacatgtc   1260
atccatgagt catagtgtgt atatctcaac attgcaaagc tacctttttt ctattatact   1320
tttcgcatta taggctagat attatctata catgtcaaca aactctatcc ctacgtcata   1380
tctgaagatt cttttcttca ctatataagt tggcttccct gtcattgaac               1430

<210> SEQ ID NO 3
<211> LENGTH: 70
<212> TYPE: DNA
<213> ORGANISM: Artificial Sequence
<220> FEATURE:
<223> OTHER INFORMATION: 5'UTR

<400> SEQUENCE: 3
tcacatcaag tttccaacaa caacaacaac aacaacaaca acaacaacaa caacaaagct    60
tctagaagcc                                                          70

<210> SEQ ID NO 4
<211> LENGTH: 72
<212> TYPE: DNA
<213> ORGANISM: Artificial Sequence
<220> FEATURE:
<223> OTHER INFORMATION: Signal peptide

<400> SEQUENCE: 4
atggccacca ttgcgttctc ccggctgtcc atctacttct gcgtgctgct gctgtgccac    60
ggctccatgg cc                                                        72

<210> SEQ ID NO 5
<211> LENGTH: 642
<212> TYPE: DNA
<213> ORGANISM: Artificial Sequence
<220> FEATURE:
<223> OTHER INFORMATION: CDS of Rituximab light chain

<400> SEQUENCE: 5
cagattgtgc tgtcccagag cccggccatc ctgtccgcga gccgggcga gaaagtgacc      60 atgacctgcc gggcgtcctc ctccgtgtcc tacatccatt ggttccagca gaagccgggc    120
```

```
tccagcccaa agccctggat ctatgccacc tccaacctgg cgtccggcgt gccggtgcgg      180
ttctccggct ccggctccgg cacctcctac tccctcacca tctcccgggt tgaggccgag      240
gatgccgcca cctactactg ccagcagtgg acctccaacc ctcccacctt cggcggcggc      300
accaagctgg agatcaagcg gaccgttgcc gcgccctccg tgttcatctt ccctcccctcc     360 gatgagcagc tcaagtccgg caccgcgtcc gttgtgtgcc tgctcaacaa cttctaccct     420
cgggaggcca aagtgcagtg gaaagttgac aatgcgctgc agtccggcaa ctcccaggag     480
tccgtgaccg agcaggactc caaagactcc acctactccc tgtcctccac cctcacgctc     540
tccaaagccg actatgagaa gcacaaagtg tatgcgtgcg aggtgaccca ccagggcctg     600
tccagcccgg tgaccaagtc cttcaaccgt ggcgagtgct ga                        642
```

<210> SEQ ID NO 6
<211> LENGTH: 1356
<212> TYPE: DNA
<213> ORGANISM: Artificial Sequence
<220> FEATURE:
<223> OTHER INFORMATION: CDS of Rituximab heavy chain

<400> SEQUENCE: 6

```
caggtgcagc tgcagcagcc gggcgccgag ctggtgaagc cgggcgcgtc cgtgaagatg      60
tcctgcaaag cgtccggcta caccttcacc tcctacaaca tgcattgggt gaagcagacg     120
ccgggccgtg gcctggagtg gattggcgcc atctacccgg gcaatggcga cacctcctac     180
aaccagaagt tcaaaggcaa agccaccctc accgccgaca gtcctcctc caccgcgtac     240 atgcagctgt cctccctcac ctccgaggac tccgccgtgt actactgcgc gcggtccacc     300
tactatggcg gcgactggta cttcaatgtg tggggcgccg gcaccaccgt gaccgtgtcc     360
gccgcgtcca ccaaagggcc ctccgtgttc cctctggcgc cctcctccaa gtccacctcc     420
ggcggcaccg ccgcgctggg ctgcctggtg aaagactact cccgagcc ggtgaccgtg     480 tcctggaact ccggcgcgct cacctccggc gtgcacacct cccggccgt gctgcagtcc     540 tccggcctgt actccctgtc ctccgttgtg accgtgccct cctcctcct gggcacccag     600 acctacatct gcaatgtgaa ccacaagccc tccaacacca agttgacaa gaaagccgag     660 cccaagtcct gcgacaagac ccacacctgc cctccctgcc cggcgccgga gctgctgggc     720
gggccctccg tgttcctgtt ccctcccaag cccaaagaca ccctcatgat ctcccggacg     780
ccggaggtga cctgcgttgt tgttgatgtg tcccatgagg acccggaggt gaagttcaac     840
tggtatgttg atggcgtgga ggtgcacaat gccaagacca gcctcggga ggagcagtac     900 aactccacct accgggttgt gtccgtgctc accgtgctgc accaggactg gctcaatggc     960
aaagagtaca agtgcaaagt gtccaacaaa gcgctgccgg cgcccattga gaagaccatc    1020
tccaaagcca aaggccagcc tcgggagcct caggtgtaca ccctgcctcc ctcccgggat    1080
gagctgacca gaaccaggt gtccctcacc tgcctggtga aaggcttcta tccctccgac    1140
attgccgttg agtgggagtc caatggccag ccggagaaca actacaagac cacgcctccg    1200
gtgctggact ccgatggctc cttcttcctg tactccaagc tcaccgttga caagtcccgg    1260
tggcagcagg gcaatgtgtt ctcctgctcc gtgatgcatg aggcgctgca caaccattac    1320
acccagaagt ccctgtccct gagcccgggc aagtga                              1356
```

<210> SEQ ID NO 7
<211> LENGTH: 265
<212> TYPE: DNA

<213> ORGANISM: Agrobacterium tumefaciens
<220> FEATURE:
<223> OTHER INFORMATION: NOS terminator

<400> SEQUENCE: 7

```
gaatttcccc gatcgttcaa acatttggca ataaagtttc ttaagattga atcctgttgc    60
cggtcttgcg atgattatca tataatttct gttgaattac gttaagcatg taataattaa   120
catgtaatgc atgacgttat ttatgagatg ggttttatg attagagtcc cgcaattata   180
catttaatac gcgatagaaa acaaaatata gcgcgcaaac taggataaat tatcgcgcgc   240
ggtgtcatct atgttactag atcgg                                         265
```

<210> SEQ ID NO 8
<211> LENGTH: 237
<212> TYPE: PRT
<213> ORGANISM: Artificial Sequence
<220> FEATURE:
<223> OTHER INFORMATION: Light chain of Rituximab with GluB-4 SP

<400> SEQUENCE: 8

```
Met Ala Thr Ile Ala Phe Ser Arg Leu Ser Ile Tyr Phe Cys Val Leu
1               5                   10                  15

Leu Leu Cys His Gly Ser Met Ala Gln Ile Val Leu Ser Gln Ser Pro
            20                  25                  30

Ala Ile Leu Ser Ala Ser Pro Gly Glu Lys Val Thr Met Thr Cys Arg
        35                  40                  45

Ala Ser Ser Ser Val Ser Tyr Ile His Trp Phe Gln Gln Lys Pro Gly
    50                  55                  60

Ser Ser Pro Lys Pro Trp Ile Tyr Ala Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Arg Val Glu Ala Glu Asp Ala Ala Thr Tyr Tyr Cys Gln
            100                 105                 110

Gln Trp Thr Ser Asn Pro Pro Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 9
<211> LENGTH: 475
<212> TYPE: PRT
<213> ORGANISM: Artificial Sequence
<220> FEATURE:
<223> OTHER INFORMATION: Heavy chain of Rituximab with GluB-4 SP

<400> SEQUENCE: 9

```
Met Ala Thr Ile Ala Phe Ser Arg Leu Ser Ile Tyr Phe Cys Val Leu
1               5                   10                  15

Leu Leu Cys His Gly Ser Met Ala Gln Val Gln Leu Gln Gln Pro Gly
            20                  25                  30

Ala Glu Leu Val Lys Pro Gly Ala Ser Val Lys Met Ser Cys Lys Ala
        35                  40                  45

Ser Gly Tyr Thr Phe Thr Ser Tyr Asn Met His Trp Val Lys Gln Thr
    50                  55                  60

Pro Gly Arg Gly Leu Glu Trp Ile Gly Ala Ile Tyr Pro Gly Asn Gly
65                  70                  75                  80

Asp Thr Ser Tyr Asn Gln Lys Phe Lys Gly Lys Ala Thr Leu Thr Ala
                85                  90                  95

Asp Lys Ser Ser Ser Thr Ala Tyr Met Gln Leu Ser Ser Leu Thr Ser
            100                 105                 110

Glu Asp Ser Ala Val Tyr Tyr Cys Ala Arg Ser Thr Tyr Tyr Gly Gly
        115                 120                 125

Asp Trp Tyr Phe Asn Val Trp Gly Ala Gly Thr Thr Val Thr Val Ser
    130                 135                 140

Ala Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Ala Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415
```

-continued

```
Asn Asn Tyr Lys Thr Thr Pro Pro Val Leu Asp Ser Asp Gly Ser Phe
            420             425             430

Phe Leu Tyr Ser Lys Leu Thr Val Asp Lys Ser Arg Trp Gln Gln Gly
            435             440             445

Asn Val Phe Ser Cys Ser Val Met His Glu Ala Leu His Asn His Tyr
            450             455             460

Thr Gln Lys Ser Leu Ser Leu Ser Pro Gly Lys
465             470             475
```

EXPRESSION VECTOR AND METHOD FOR THE STABLE PRODUCTION OF A PROTEIN IN A PLANT, IN PARTICULAR A WHOLE RECOMBINANT ANTIBODY IN A CEREAL ENDOSPERM

SEQUENCE LISTING

The instant application contains Sequence Listing which has been submitted via EFS-Web and is hereby incorporated by reference in its entirety. Said Sequence Listing, created on Apr. 14, 2017, is named Sequence-Listing-Created-April-14-2017.txt and is 31,000 Bytes in size.

CROSS-REFERENCE TO RELATED APPLICATIONS

This application is a National Phase Application of International Application PCT/IT2018/050065 filed on Apr. 16, 2018, which claim priority to Italian Application No. 102017000042052 filed on Apr. 14, 2017, the entire contents of which are incorporated herein by reference.

FIELD OF THE INVENTION

Embodiments described here concern genetic engineering operations intended for the industrial production of pharmaceutical proteins in plants, in particular the synthesis and accumulation of whole antibodies inside the endosperm of cereal species. In particular, embodiments described here concern an expression vector and method for the stable production of a protein, which can be human or animal, in plants, in particular a whole recombinant antibody in cereal endosperm.

BACKGROUND OF THE INVENTION

It is known that, together with hormones, cytokines and vaccines, antibodies are one of the main classes of biopharmaceuticals registered for therapeutic and diagnostic use. If the biopharmaceuticals still in the development phase are considered, antibodies in their entirety take on an even greater significance. Antibodies or immunoglobulins (IgG) are proteins with a quaternary structure consisting of four polypeptide chains, two of which are heavy (H) and two are light (L), identical to each other; in the framework of the immune system, they have the function of neutralizing foreign bodies such as viruses and bacteria, by recognizing portions of macromolecules known as antigenic determinants or epitopes. Alongside whole antibodies, several antibody-like molecules have been developed, including Fab fragments (acronym of fragment antigen binding), scFv (acronym of single chain fragment variable), scFv dimers, mini-antibodies, domains of single variable chains.

Thanks to their characteristics, antibodies are widely used in the prevention, detection and treatment of numerous human pathologies (for example arthritis, tumors, autoimmune diseases, inflammatory states). The development of recombinant antibodies has paved the way for passive immunization of patients at risk, an interesting therapeutic alternative if we consider the increased frequency of antibiotic-resistant bacterial strains and the appearance of new pathogens.

The production on an industrial scale of recombinant antibodies is essentially based on the sterile culture of genetically transformed mammalian cells in suitable bioreactors; in particular, the CHO system (acronym of Chinese hamster ovary cells) is among the most widespread due to its ability to originate correctly assembled whole antibodies equipped with a human-compatible glycosylation profile. However, this system presents many problems, including: high investment and operating costs, slowness in reaching the final production scale and potential risk of contamination of the cultures and products with pathogenic organisms (bacteria, viruses, *mycoplasma*), toxins and prions.

In spite of the optimistic projections presented on several occasions by the industries operating in the sector, the price per milligram (mg) of antibody has remained almost constant over the last decade, so much so that the Italian Medicines Agency, in line with the European Medicines Agency, has called for the development of alternative systems for large-scale production (AIFA, 2013).

The potential offered by plants in the production of recombinant proteins has been known for a long time and is widely documented (Giddings, 2001; Obembe et al., 2011; Stoeger et al., 2014). Although no recombinant antibody produced from a plant has so far been registered for clinical use, there is numerous experimental evidence to show the effective production capacity of IgG by plant species (Hiatt et al., 1989; During et al., 1990; Conrad and Fiedler, 1994; Ma et al., 1998; Ma et al., 2003; Nicholson et al., 2005; Stoeger et al., 2005; Ramessar et al., 2008; Villani et al., 2009; De Muynck et al., 2010; Vamvaka et al., 2016). E. Torres et al. (2001) also describes the accumulation of recombinant and non-recombinant proteins in plants.

In the current state of the art, in terms of expression within the host cell, the light polypeptide chains L and heavy polypeptide chains H are considered separately so that the molecular vectors that carry the genetic information relating to their synthesis are distinct and/or the elements that control the transcription and translation of the coding sequences do not coincide with each other. Therefore, although the light chains L and heavy chains H are recognized as being part of a molecule with a quaternary structure, the corresponding molecular expression cassettes are constructed, in the state of the art, independently and the procedures for the genetic transformation of the plants are those normally used to express two proteins that are structurally and functionally not correlated. The table shown in FIG. 13 shows the general scheme of composition of the sequences encoding for the polypeptide chain L (CDS-L) and H (CDS-H).

According to the state of the art, upstream of each CDS (Coding Sequence) a promoter and a leader sequence are located, while downstream there is a terminator; the nature and the particular characteristics of the regulation elements of the expression of the CDS are variable in the vectors used, also depending on the host plant and the tissue in which the final expression of the antibody is intended to be made. Expression cassettes are included inside plasmid or viral vectors used in the genetic transformation of plants using physical or biological methods. Almost always the host plant species is represented by *Nicotiana* spp. and the final antibody is expressed in leaves, in particular in the cells of the leaf mesophyll; the subcellular localization of the recombinant antibody can correspond to the lumen of the endoplasmic reticulum, the apoplast or the vacuole.

According to the state of the art, the co-presence inside the same cell of light L and heavy H chains is obtained through co-transformation (that is, by the joint use of different molecular vectors) or, alternatively, through transformation of plants by the separate expression of one or the other chain (disjointed use of molecular vectors) followed by hybridization between plants of different types. FIG. 14 shows the most widely used schemes to obtain the combined presence of the H and L chains in the host cell. These are procedures that put the molecular cassettes necessarily or potentially in a trans configuration.

Regardless of the procedure used, however, scientific and technical literature generally shows positive results: recombinant antibodies are in fact produced by the transformed plants, and are able to recognize and bind the target antigen. Also with reference to the antibody yield, the data obtained in the plant are considered satisfactory.

There is, however, a need to significantly increase the yield of antibody obtained in the plant, to obtain a simplification of the selection procedures of the production line and a more rapid development path of the antibody usable for diagnostic or therapeutic purposes.

In the state of the art, different strategies are used to obtain whole antibodies in the plant, each of which includes critical factors of common and specific type. In order to show them, it is useful to first examine the methodology that envisages the transformation of plants with vectors carrying genetic information for the disjoint synthesis of each polypeptide chain (H, L) inside different primary transformants; to obtain the whole antibody, hybrids are obtained by crossing the pure homozygous lines generated by self-fertilization or production of haploid types from the primary transformants. This procedure, even if widely used in particular monocot and dicot species, has different counter-indications to the extent that it entails: 1. a more difficult work to select the primary transformants (also complicated by the need to adopt different detection methods for each chain); 2. the burden of fixing the homozygous state of the individual transgenes and this in the absence of evidence of production of the whole antibody correctly assembled and biologically active; 3. the execution of controlled manual crosses to make hybrids; 4. further selection interventions intended to release the final homozygous production line for both transgenes.

A variant of the method described above entails the production of hybrids by crossing the primary transformants and the subsequent selection of the progenies by detection of the whole antibody. If in a purely technical sense the work is very simplified, it is not so from a methodological point of view because the primary transformants are always hemizygous for the transgenes and this condition can be multiple if there are several genomic insertion sites present. In the absence of a preliminary knowledge of the crossing parents, it becomes necessary to greatly widen the selection program because: each crossing parent produces different gametes; the random union of gametes leads to the formation of a dis-homogeneous progeny; this progeny will in turn produce a variable progeny due to segregation in an independent or associated form of the transgenes.

A second strategy used to produce antibodies in plants provides to apply co-transformation methods for the simultaneous insertion of transgenes from different vectors. Compared to the variant described above, this procedure allows to save the time of one generation; however, it keeps the methodological limitations with the aggravating circumstance that the transgenes frequently co-integrate in the same chromosomal site, generating inverse or direct tandem structures triggering gene silencing processes (Meyer and Saedler, 1996; Ye and Signer, 1996; Muskens et al., 2000; Stam et al., 2000; Wang and Waterhouse, 2000; De Buck et al., 2001; Ma and Mitra, 2002; Lechtenberg et al., 2003; Fojtova et al., 2006; Skarn et al., 2006; Mlotshwa et al., 2010; Otagaki et al., 2011; Martinez De Alba et al., 2013; Ramkumar et al., 2015). Moreover, a restructuring of the molecular expression cassettes with loss or acquisition of sections is more probable; these events are identified only through complete genomic sequencing and cause the abandonment of the production line due to the lack of the necessary regulatory requirements. In particular, in order to develop production lines that can be used on an industrial level for the synthesis of antibodies, the co-transformation methods based on physical agents (biolistics, electroporation) appear quite unsuitable since they often determine the insertion of multiple copies of the transgene in multiple insertion sites. An example of a biolistic method is described in Rademacher et al., 2008.

To summarize, co-transformation with the joint use of molecular vectors for the combined expression of the H and L chains can result in the formation of trans or cis configurations, but in both cases the expression of the whole antibody and the selection of the production line will be problematic because of a production imbalance of the chains and the establishment of gene silencing phenomena.

Other technical solutions provide the production of IgG with viral expression vectors or the transitory synthesis of the antibody following infiltration of leaf tissues with engineered strains of *Agrobacterium*. These methods not only have problems of biosafety and authenticity of the polypeptide chains produced, but also they are not covered by current European legislation which is able to evaluate only the quality of the methods and biotechnological products inherent to the stable transformation of higher sporophyte plants (angiosperms and gymnosperms) (EMA, 2008). This determines a substantial irrelevance of the methods described above in terms of industrial applicability.

Zhong Huang et al. (2010) describes viral expression vectors used for transient expression in leaves of *Nicotiana benthamiana*.

On the basis of these premises, it should be noted that it is desirable that the final production line expresses high and basically equimolar quantities of the two polypeptide chains H and L inside the same cell compartments. A strong quantitative discrepancy between the two chains, in fact, inevitably leads to a reduction in the final yield of antibody due to the lack of one of the two components and possible interferences in the assembly thereof with the production of aberrant molecules. Among the factors able to determine a different level of expression of the H and L chains there are: the insertion site of the transgene (position effect), the number of copies of the transgene, the particular composition of the molecular expression cassettes.

FIG. 15 schematically shows an example of position effect: the transgenes carrying the information for the synthesis of the L and H chains are differently expressed due to the interference generated by enhancer elements (E), silencers (S) and regions containing methylated DNA (ME).

As previously shown, the use of repeated exogenous DNA sequences or their formation following the insertion of multiple copies of one or both transgenes causes the silencing of the segments inserted or, in less unfavorable but still negative situations, a reduction and an instability of expression of the transgenes. These phenomena occur irrespective of the position of insertion in the genome and are connected to the generation of inverse but also direct tandem repeats. In the current state of the art it is therefore expected that, if it is intended to produce whole antibodies in plants, vectors carrying expression cassettes will be used, characterized by a different composition of the control elements of gene expression (promoters, 5'-UTR, 3'-UTR). This solution, in the state of the art perceived necessary in view of an effective expression of the transgenes, nevertheless entails a considerable difficulty in obtaining pure and stable lines endowed with high production potential. In fact, it is known that every component of the molecular cassette is able to influence in a different and specific way the level of expression of a transgene, to the point that it is difficult to program, and even more obtain, a contemporary and coordinated expression of polypeptide chains H and L. The problem becomes even more evident if we consider that the expression cassettes each consist of several interdependent components and differently active as the physiological conditions of the plant or of the tissue in which the antibody expression is obtained change. In particular, the inducible promoters are differently activated by a common induction factor or by different inducers, the tissue-specific ones do not show the same phase-dependence nor the same transcriptional activity, while the constitutive promoters show a variable transcriptional strength depending on the organ, the tissue, the stage of development and the growth conditions of the plant.

There is therefore a need to perfect an expression vector and a method for the stable production of a plant protein, in particular a whole recombinant antibody in cereal endosperm that can overcome at least one of the disadvantages of the state of the art.

In particular, one purpose of the present invention is to perfect an expression vector and a method for the industrial production of a whole antibody in plants, especially a monocotyledonous plant, in particular inside the endosperm of a cereal species, which improves the features referred to in the state of the art with reference to the number and type of vectors used, the selected vector system, the gene silencing resulting from the presence of repeated DNA sequences in inverse but also direct tandem structures, the genetic transformation modalities as well as the control elements of gene expression used for the synthesis of light L and heavy H polypeptide chains; this in order to obtain a high expression and a specific tissue and sub-tissue localization of the relevant antibody molecule.

The Applicant has devised, tested and embodied the present invention to overcome the shortcomings and improve the features of the state of the art and to obtain a more efficient system for the production of recombinant antibodies usable on an industrial level for the production of therapeutic molecules.

SUMMARY OF THE INVENTION

The present invention is set forth and characterized in the independent claims, while the dependent claims describe other characteristics of the invention or variants to the main inventive idea.

In accordance with some embodiments, an expression vector is provided for the stable production of a protein, which can be human or animal, in plants, in particular a whole recombinant antibody in a cereal endosperm. According to one embodiment the expression vector is a single vector that comprises:
  an expression cassette for the light polypeptide chain (L) of the antibody,
  an expression cassette for the heavy polypeptide chain (H) of the antibody, having the same orientation and the same regulatory elements of gene expression.

In accordance with possible embodiments, the expression cassettes of the light polypeptide chain (L) and the heavy polypeptide chain (H):
a) are operatively linked, in particular they are inserted according to the same head-to-tail orientation, inside a DNA segment that is inserted integrally into the genome of a plant;
b) each are provided with the following regulatory elements of the gene expression:
i) an endosperm-specific promoter of natural or artificial origin,
ii) a leader sequence (5'-UTR) of natural or artificial origin;
iii) a signal peptide of natural or artificial origin to transit the recombinant polypeptide chain inside the lumen of the endoplasmic reticulum of the cells that make up the endosperm,
iv) a nucleotide sequence of natural or artificial origin encoding the mature form of the polypeptide chain, respectively light (L) or heavy (H), of the antibody;
v) a trailer sequence (3'-UTR) of natural or artificial origin, wherein the regulatory elements of gene expression i), ii), iii) and v) are identical between said expression cassettes of the light polypeptide chain (L) and the heavy polypeptide chain (H).

In accordance with other possible embodiments the cereal is rice.

Furthermore, in accordance with possible embodiments, the endosperm-specific promoter i) of natural or artificial origin is the promoter of the gene for rice glutelin 4 (GluB-4), as indicated in SEQ ID NO: 2.

In accordance with some embodiments the region 5'-UTR ii) is of synthetic nature and is characterized by repeated CAA trinucleotide elements and by a consensus sequence AGCCATGGC for the recognition of the translation start site as indicated in SEQ ID NO: 3.

In accordance with other embodiments, the nucleotide sequence of the signal peptide iii) corresponds to the sequence as indicated in SEQ ID NO: 4, encoding the signal peptide used in rice to convey the glutelin 4 precursor inside the endoplasmic reticulum (PSGluB-4).

In possible embodiments, the trailer sequence 3'-UTR v) is the NOS terminator, whose sequence is indicated in SEQ ID NO: 7, or the terminator of the rice GluB-4 gene.

In accordance with other embodiments, the nucleotide sequences iv) encoding the mature form of the polypeptide chain, respectively light (L) or heavy (H), of the antibody are represented by the sequences encoding the light (L) and heavy (H) polypeptide chain of the antibody Rituximab, as indicated respectively in SEQ ID NO: 5 and SEQ ID NO: 6.

In other possible embodiments, the sequences encoding the light (L) and heavy (H) polypeptide chain are optimized for expression in plants through the use of preferential species-specific synonymous codons.

In other possible embodiments, the expression vector comprises a gene able to allow the selection of the transformed plants, in particular a PMI (phospho-mannose isomerase) selection cassette.

In other possible embodiments, the vector comprises an expression cassette for selection of transformed plant cells containing:
  a constitutive promoter of natural or artificial origin,
  a coding sequence for the selected marker in its natural or artificial synonymous version,
  a terminator of natural or artificial origin suitable for a plant expression system.

In other possible embodiments, the single expression vector has the sequence indicated in SEQ ID NO: 1.

In accordance with other embodiments, a bacterial strain is provided comprising an expression vector according to the present description. In possible implementations, the bacterial strain is a strain of *Agrobacterium tumefaciens* or *A. rhizogenes*.

In accordance with other embodiments, a binary transformation system mediated by *Agrobacterium* spp. is provided, consisting of an expression vector in accordance with the present description and a complementary vector bearing the Vir region for the construction of a binary transformation system.

According to other embodiments, stably transformed plant cells, plants and plant seeds are provided, obtained by means of an expression vector in accordance with the present description. In possible implementations, the plant cells, plants and plant seeds are for direct or indirect use in therapeutic treatment.

Other embodiments concern a method for the stable production of a protein, which can be human or animal, in plants, in particular a whole recombinant antibody in a cereal endosperm, said method comprising:
construction of a molecular vector for the genetic transformation of plants in accordance with the present description,
industrial processing of the transformed seed,
extraction and purification of the antibody of interest.

Advantageously, the yield of whole recombinant antibody stably produced can be more than 0.6 grams, in particular more than about 0.7 grams, more particularly more than about 0.8 grams, even more particularly more than about 0.9 grams of antibody per kilogram of endosperm.

By the expression "about" we mean a possible variability of 20% more or less than the values indicated.

Possible example yield values of antibody are for example 0.8, 0.85, 0.9, 0.95, 1, 1.05, 1.15, 1.2, 1.25, 1.3 grams, or more of antibody per kilogram of endosperm.

Advantageously, in the case of Rituximab the yield can be greater than about 0.9 grams of Rituximab per kilogram of endosperm. For example, the yield of Rituximab can vary from about 0.9 to about 1.5 grams, in particular from about 0.95 to about 1.2 grams of Rituximab per kilogram of endosperm.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some embodiments, given as a non-restrictive example with reference to the attached drawings wherein:

FIG. 3 shows the amino acid sequence of the light (A; corresponding to SEQ ID NO: 8) and heavy (B; corresponding to SEQ ID NO: 9) chain of Rituximab; the GluB-4 signal peptide is highlighted;

FIG. 7 shows the result of electrophoretic analysis. In particular:

FIG. 10 shows the signals recorded in MALDI-TOF relating to the glycoforms released by the heavy chain following treatment with PNGase A, the corresponding composition in monosaccharides and the description of the probable structure;

FIGS. 11a and 11b show respectively:

FIG. 11a. the results of cytofluorimetric analyses (FACS) performed on: A. 500,000 MEC-1 cells; B. MEC-1 cells in the presence of commercial Rituximab; C. MEC-1 cells in the presence of RTX PBS (purified antibody from rice);

FIG. 11b. the mean fluorescence intensity given by the commercial antibody Rituximab and the purified antibody from rice. FL1-H: fluorescence intensity;

DETAILED DESCRIPTION OF SOME EMBODIMENTS

Figure 1A:
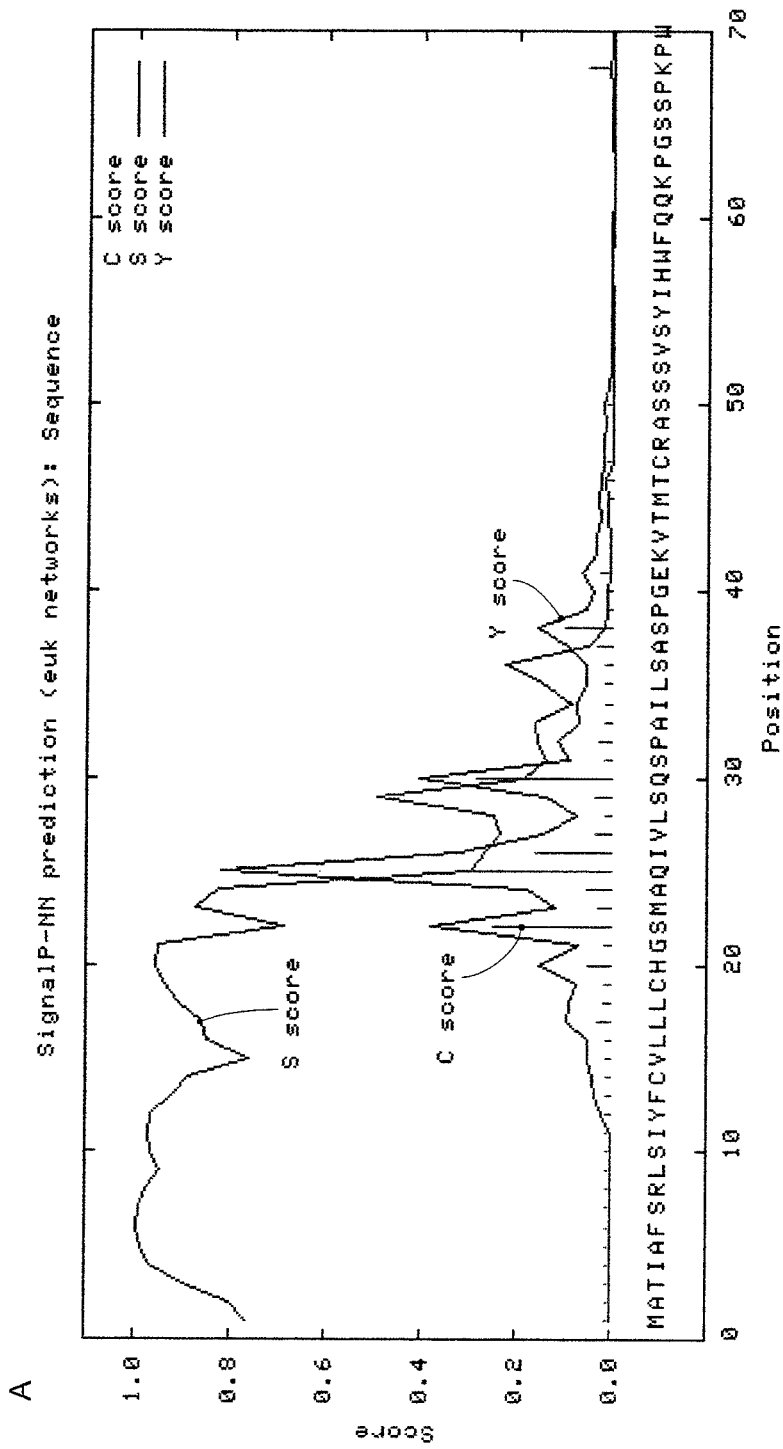
FIGS. 1a and 1b show the prediction of the cleavage site between the PS of GluB-4 and the polypeptide chains L (section A) and H (section B) through the SignalP 3.0 software.

We will now refer in detail to the various embodiments of the present invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

Before describing these embodiments, it is necessary to clarify that the present description is not limited in its application to details of the construction and disposition of the components as described in the following description using the attached drawings. The present description can provide other embodiments and can be obtained or executed in various other ways. It is also necessary to clarify that the phraseology and terminology used here is for the purposes of description only, and cannot be considered as limitative.

Unless otherwise defined, all the technical and scientific terms used here and hereafter have the same meaning as commonly understood by a person with ordinary experience in the field of the art to which the present invention belongs. Even if methods and materials similar or equivalent to those described here can be used in practice and in the trials of the present invention, the methods and materials are described hereafter as an example. In the event of conflict, the present application shall prevail, including its definitions. The materials, methods and examples have a purely illustrative purpose and shall not be understood restrictively.

All the measurements are carried out, unless otherwise indicated, at 25° C. and at atmospheric pressure. All the temperatures, unless otherwise indicated, are expressed in degrees Celsius.

All the percentages and ratios indicated are intended as referring to the weight of the total composition (w/w), unless otherwise indicated.

Embodiments described here refer to the field of molecular farming and deal in particular with the development of a method, in particular the construction of a stable expression vector in plants, for the production of whole antibodies in cereal endosperm, for example rice.

Other embodiments described here concern a plasmid vector able to direct the plant expression of both the structural components of an antibody molecule, that is, the light (L) and heavy (H) polypeptide chain.

According to some embodiments, the expression vector was made for the endosperm-specific expression of glycosylated whole antibodies in cereal seed. In particular, in order to make the vector we considered aspects concerning the genetic transformation of plants, the control elements of gene expression (promoter, leader region, terminator), the sequences encoding the polypeptide chains H and L, the sequences encoding the signal peptides.

The present invention therefore proposes a method that allows a rather significant increase in the yield of whole antibody in plants, a considerable simplification of the selection procedures of the production line and a more rapid development path of the antibody usable for diagnostic or therapeutic purposes.

The present invention is the result of inventive activity to the extent that it responds to specific technical problems never previously identified, nor fortuitously resolved directly or indirectly by those who have worked in the field of molecular farming.

The present invention represents the result of experimental tests carried out by the Applicant and planned in the perspective of a co-localized and coordinated expression of the polypeptide chains L and H, which, according to the present invention, are no longer intended as separate precursor elements but as closely related factors starting from their cell synthesis.

In order to offer a new and inventive technical solution to the need for interdependence in synthesis, the Applicant has devised and implemented a molecular vector in which the molecular cassettes related to the L and H chains:
a) are operatively linked inside a segment of DNA that is integrally inserted into the genome of a plant;
b) are provided with the same control and regulation elements of gene expression: promoter, 5'-UTR, terminator;
c) have the same orientation.

Advantageously, moreover, to solve the problems of expression instability and gene silencing associated with the presence of repeated DNA sequences in tandem inside the genome of a plant, the Applicant has further carried out experimental tests to identify a plant tissue in which these phenomena do not exist, thus identifying a technical solution represented by synthesis inside the endosperm of cereal species.

The vector system was chosen in the perspective of a genetic transformation of plants that can be achieved by *Agrobacterium tumefaciens* or *A. rhizogenes*; therefore, a T-DNA vector (abbreviation of Transfer DNA) was constructed, configured to complement a second plasmid carrying the Vir region for the formation of a binary transformation system.

In possible embodiments, the vector carrying the T-DNA according to the present disclosure can be characterized by a replication origin with a high number of copies in *Escherichia coli*.

In possible embodiments, the vector carrying the T-DNA according to the present description can be characterized by the presence of a replication origin suitable to confer a high stability in *Agrobacterium* spp. (e.g. pVS1).

In possible embodiments, the vector carrying the T-DNA according to the present description can be characterized by small dimensions (<10 kb).

In possible embodiments, the vector carrying the T-DNA according to the present description can be characterized by the presence of restriction sites suitable for a modular modification of the plasmid.

In possible embodiments, the vector carrying the T-DNA according to the present description can be characterized by the presence of a multiple cloning site.

In possible embodiments, the vector carrying the T-DNA according to the present description can be characterized by the presence of a gene able to allow the selection of the transformed bacteria (e.g. npt II, encoding for the enzyme neomycin phosphotransferase of type II, for the identification of positive colonies with kanamycin).

In possible embodiments, the vector carrying the T-DNA according to the present description can be characterized by the presence of a gene able to allow the selection of the transformed plants (for example PMI, encoding for the enzyme phospho-mannose isomerase, for the identification of embryogenic calli transformed with mannose).

In possible embodiments, the vector carrying the T-DNA according to the present description can be characterized as being T-DNA, that is, a segment of the plasmid in which the expression cassettes of the transgenes are located for their whole transfer into the genome of the host plant.

In possible embodiments, the vector carrying the T-DNA according to the present description can be characterized by repeated sequences LBR (Left Border Region) and RBR (Right Border Region), respectively at the left and right margin of the T-DNA.

Advantageously, according to possible embodiments, the nucleotide sequence of the expression vector is as indicated in SEQ ID NO: 1.

With regard to the control elements of the gene expression, the T-DNA of the vector according to the present description contains inside it three expression cassettes, one of which relating to the selection of the transformed plants or plant cells and two relating to the polypeptide chains H and L that make up the antibody.

According to one or more embodiments in accordance with the present description, the expression cassette for the selection of the transformed plant or plant cells comprises: a constitutive promoter of natural or artificial origin, a coding sequence for the selected marker in its natural version or artificial synonym and a terminator of natural or artificial origin provided it is suitable for a plant expression system.

According to an advantageous embodiment, the constitutive promoter is 35S of CaMV, the sequence encoding the marker is the one relating to the enzyme phospho-mannose isomerase of *E. coli* (Gene Bank access number M15380) and the terminator is 35 Ster of CaMV.

According to one embodiment, the expression cassettes relating to the antibody chains have a similar structure, being equipped with the following regulatory elements of gene expression: i. an endosperm-specific promoter of natural or artificial origin; ii. a leader sequence 5'-UTR of natural or artificial origin; iii. a peptide signal of natural or artificial origin to send the recombinant polypeptide chain into the lumen of the endoplasmic reticulum of the cells that make up the endosperm and for its tissue accumulation; iv. nucleotide sequences of natural or artificial origin each encoding the mature form of the light and heavy polypeptide chain of the antibody; v. a trailer sequence 3'-UTR of natural or artificial origin.

According to some embodiments described here, the regulatory elements of gene expression i), ii), iii) and v) are the same in the expression cassettes of the light polypeptide chain and of the heavy polypeptide chain.

According to one embodiment, the promoter i) is the glutelin 4 promoter of rice (GluB-4), whose sequence is indicated in SEQ ID NO: 2.

According to an advantageous embodiment, the leader sequence 5'-UTR ii) is of a synthetic nature and is characterized by repeated CAA trinucleotide elements and by a consensus sequence for the recognition of the initial translation site, for example specific for rice (AGCCATGGC), whose sequence is indicated in SEQ ID NO: 3.

For example, the leader sequence 5'-UTR can contain a large number of repeated CAA trinucleotide elements, in particular two or more CAA trinucleotide elements, more particularly three or more, even more particularly four or more.

According to another embodiment, the nucleotide sequence of element iii) corresponds to the sequence PSGluB-4, as indicated in SEQ ID NO: 4, encoding the signal peptide used in rice to convey the glutelin 4 precursor inside the endoplasmic reticulum.

According to another embodiment, the nucleotide sequences of element iv) are represented by the sequences encoding the light and heavy chain of an antibody, for example the Rituximab antibody, as indicated in SEQ ID NO: 5 and SEQ ID NO: 6.

According to an advantageous embodiment of the invention, the trailer sequence 3'-UTR of element v) is the terminator NOS, whose sequence is indicated in SEQ ID NO: 7. Alternatively, the terminator of the GluB-4 gene of rice can be used.

The three expression cassettes are delimited by the left and right margins (LBR and RBR) of the T-DNA and have the same head-to-tail orientation.

With regard to the sequences encoding the relevant genes, in order to achieve at the DNA and RNA level structural contexts favorable to the high expression of the antibody in cereal endosperm, the sequences encoding the light (L) and heavy (H) polypeptide chain have been redefined in silico using the codon context method, that is, the use of synonymous species-specific codons; finishing interventions have also been performed to eliminate, inside the sequences, any cryptic introns, motifs associated with instability or incorrect transcription and/or unwanted restriction sites.

According to one embodiment, the expression vector is introduced into bacterial strains, which are used directly or indirectly, for the genetic transformation of the plants. Advantageously, the bacterial strain is selected from a group comprising the species *Escherichia coli*, *Agrobacterium tumefaciens* and *A. rhizogenes*. Preferably, the transformed plants are cereals. According to a preferred embodiment, the bacterial strain is used for the transformation of embryogenic calli of rice (*Oryza sativa* ssp. *japonica*, var. CR W3). It is a form of stable transformation in which the transgene integrates definitively into the genome of the plant to be expressed in the seed endosperm.

The present invention, in addition to the steps of creating the molecular vector and the genetic transformation of the plants, also comprises an industrial processing step of the transformed seed and a step of extraction and purification of the relevant antibody.

According to a possible embodiment, industrial processing provides to subject the mature seeds harvested from the transformed cereal plants, after suitable drying, to operations of dehulling and whitening to remove the fibrous component, the germ and the aleuronic layer containing contaminating proteins.

In accordance with another possible embodiment, the extraction step provides to homogenize the seed flour in a suitable saline buffer, followed by clarification through filtration and concentration through ultra-filtration; the purification step can be carried out for example by affinity chromatography with protein A followed by gel-filtration.

The embodiments according to the present description, unlike the techniques known in the state of the art, are obviously innovative and advantageous in that they allow to obtain transgenic cereal plants through stable genetic transformation, in particular of rice, able to produce and accumulate significant quantities of whole antibody in the seed endosperm using a single vector and identical regulation sequences of gene expression for the two chains; the antibody molecule is correctly assembled and consists of polypeptide chains carrying the programmed amino acid sequence, without additional amino acid residues which are useless if not harmful in terms of localization, stability, biological activity, complement activation and use in the therapeutic field. With the present invention, the antibody yield can be of the range of about 1 g or more per kg of endosperm. We believe that the yields obtained are of absolute relevance for the advantageous industrial application of the technology described here, and are significantly greater than what is reported in the state of the art.

The molecular expression cassettes necessary for the production of antibodies are advantageously inherited from the progeny according to the normal Mendelian patterns and can be easily taken in homozygosity.

According to an advantageous variant, the antibody produced is Rituximab, a monoclonal antibody that targets the epitope CD20.

As well as the expression vector and the nucleotide sequences used in the construction of the expression cassettes, the present invention also concerns their complementary sequences.

Furthermore, the present invention also concerns the sequences equivalent to those mentioned above, deriving from mutation processes, regardless of the nature, causative force and location of the mutation. Therefore, the present invention also concerns sequences obtained by deletion, insertion, transition, transversion of one or more nucleotides in any region whatsoever of the vector, expression cassettes or sequences complementary thereto.

The present invention includes combinations of the nucleotide sequences encoding the mature form of the light L and heavy H polypeptide chains with promoter elements, sequences for sending into the endoplasmic reticulum and regions not translated into 5' and 3', suitable to obtain the synthesis and the accumulation of a whole antibody molecule functioning in the seed endosperm or with nucleotide sequences complementary to said sequences.

The present invention also concerns the combination of the elements i), ii), iii), iv) and v) indicated above, with sequences encoding the light L and heavy H chain of other antibodies, or combinations made with nucleotide sequences complementary to said sequences.

The present invention also concerns the use of the expression vector as above for the transformation of a plant for the stable production of a recombinant protein, in particular of a whole recombinant antibody.

Also included in the present invention are bacterial strains comprising the expression vector described above.

Also included in the present invention are plant cells transformed with the expression vector described above. According to a possible solution of the invention, the cells are cereal cells, preferably belonging to the cultivated rice species (*Oryza sativa* L.).

The use of waxy types, exploited industrially for the extraction and production of starch and its derivatives, is also included in the invention.

Also part of the present invention is a plant seed transformed using an expression vector as described above. According to one solution of the invention, the seed is of a stably transformed plant belonging to the class of cereals, preferably the stably transformed plant belongs to the species *Oryza sativa* L.

Also within the scope of protection of the present invention is a stably transformed plant for the expression of a recombinant antibody, which is stably transformed by means of an expression vector as described above.

Also included in the present invention are the progenies obtained by self-fertilization or cross-breeding, or transformed lines selected from a plant as described above. The present invention also concerns a seed as indicated above for direct or indirect use in therapeutic treatment.

DETAILED DESCRIPTION OF SOME EMBODIMENTS

Specific embodiments according to the present description concern a method for the production of a whole antibody in cereal endosperm, in particular in rice endosperm (*Oryza sativa* L.). The method is based on the construction of a particular vector system able to host gene expression cassettes with unique characteristics of composition and assembly.

Embodiments of the method provide the stable transformation of plants using a single expression vector containing at least the following two gene cassettes, having the same head-to-tail orientation; in particular, the single expression vector comprises:
 expression cassette of the light polypeptide chain (L) of the antibody;
 expression cassette of the heavy polypeptide chain (H) of the antibody.

Furthermore, in possible implementations, the expression vector also contains a third cassette, that is, an expression cassette for the selection of the transformed plant cells.

In possible implementations, the three cassettes cited above are contained in a T-DNA region since the expression vector comprises, in association with a second plasmid, a binary transformation system mediated by *Agrobacterium*; the nucleotide sequence contained in the expression vector is, for example, as indicated in SEQ ID NO: 1.

According to a possible embodiment, the expression cassette relating to the selection of the transformed plant or plant cells comprises: a constitutive promoter of natural or artificial origin, a sequence encoding the marker in its synonymous natural or artificial version and a terminator of natural or artificial origin suitable for a plant expression system.

According to an advantageous embodiment, the constitutive promoter is 35S of CaMV, the sequence encoding the marker is the one relating to the enzyme phospho-mannose isomerase of *E. coli* (Gene Bank accession number M15380) and the terminator is 35Ster of CaMV.

According to one embodiment, the expression cassettes relating to the light (L) and heavy (H) polypeptide chains of the antibody have a similar structure; each is provided with the following control elements: i. an endosperm-specific promoter of natural or artificial origin; ii. a leader sequence 5'-UTR of natural or artificial origin; iii. a peptide signal of natural or artificial origin to address the recombinant polypeptide chain inside the lumen of the endoplasmic reticulum of the cells comprising the endosperm and for its tissue accumulation; iv. a nucleotide sequence of natural or artificial origin encoding the mature form of the chain (light or heavy) of the antibody; v. a trailer sequence 3'-UTR of natural or artificial origin.

According to possible implementations, among the possible endosperm-specific promoters of cereal and rice species in particular, it is possible to advantageously use the gene promoter for rice glutelin 4 (GluB-4), whose sequence is indicated in SEQ ID NO: 2. Advantageously, this promoter is distinguished by a higher transcriptional activity compared to promoters of other storage proteins present in the rice endosperm, such as globulins, prolamins and glutelins other than GluB-4.

The promoter GluB-4 was isolated by PCR from the waxy variety CR W3 (Ente Nazionale Risi, Milan, Italy) together with the leader region. However, the latter appeared to be rather short and poorly provided with elements able to reinforce gene expression; for this reason, it was replaced by a synthetic leader sequence 5'-UTR (as indicated in SEQ ID NO: 3) characterized by a high number of trinucleotide elements CAA (that is, elements able to increase the translational efficiency of the TMV leader Ω; Gallie and Walbot, 1992) and by a consensus recognition sequence of typical ATG for rice (AGCCATGGC; Rangan et al., 2008). The GluB-4 signal peptide (abbreviated PSGluB-4) is encoded by the nucleotide sequence reported in SEQ ID NO: 4; the latter has been advantageously placed before the sequences encoding the light (L) and heavy (H) polypeptide chains. PSGluB-4 was used to convey both chains in the lumen of the endoplasmic reticulum.

Figure 1B:
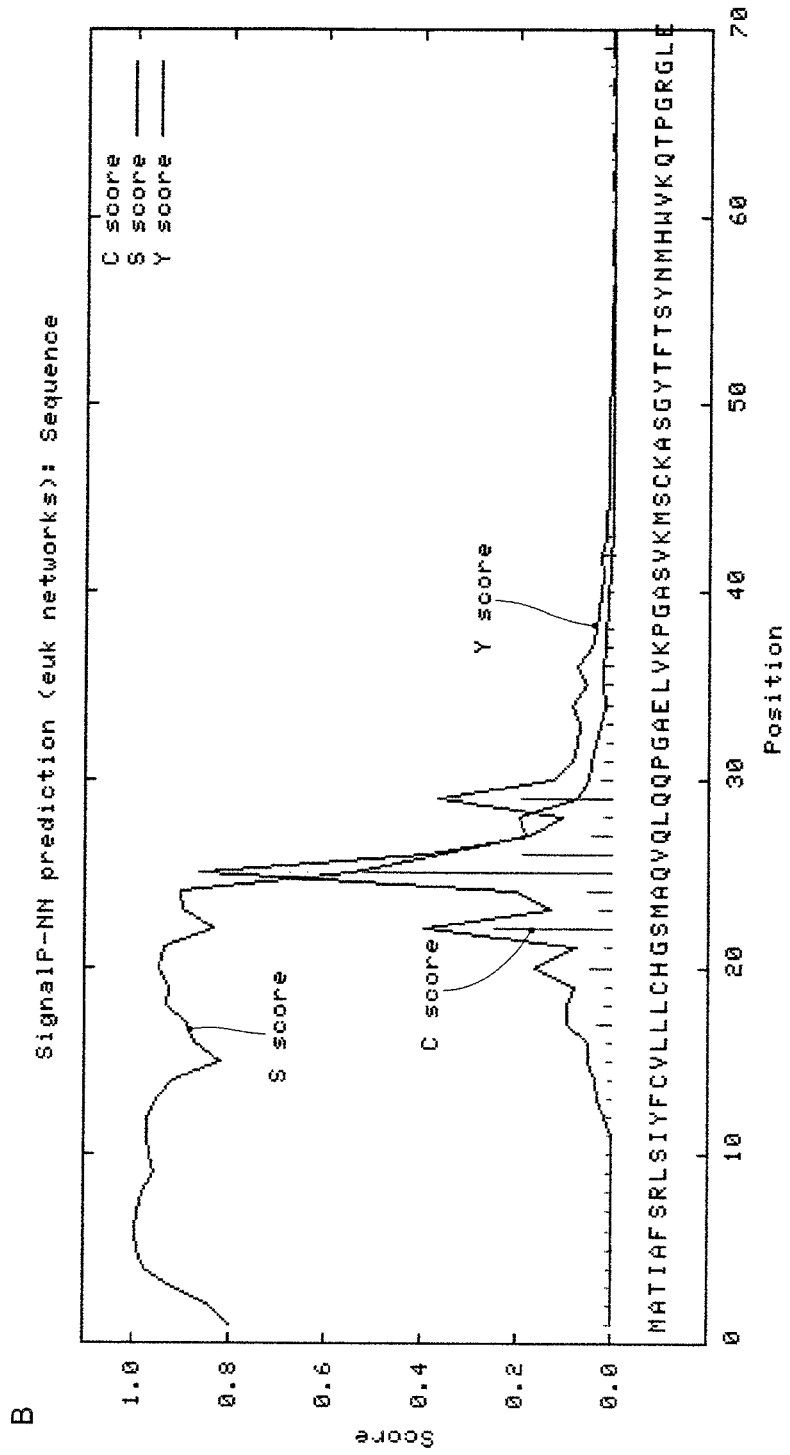
Figure 12:
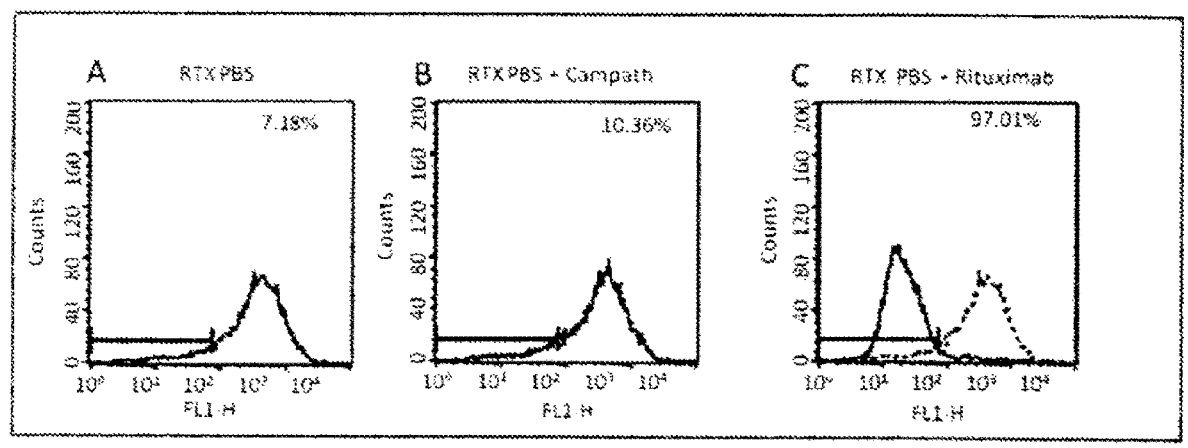
FIG. 12 shows the FACS analysis of the competition assay between RTX PBS, commercial Rituximab and a non-correlated antibody (anti-CD52, Campath), used as a negative control. FL1-H: fluorescence intensity.
Figure 13:
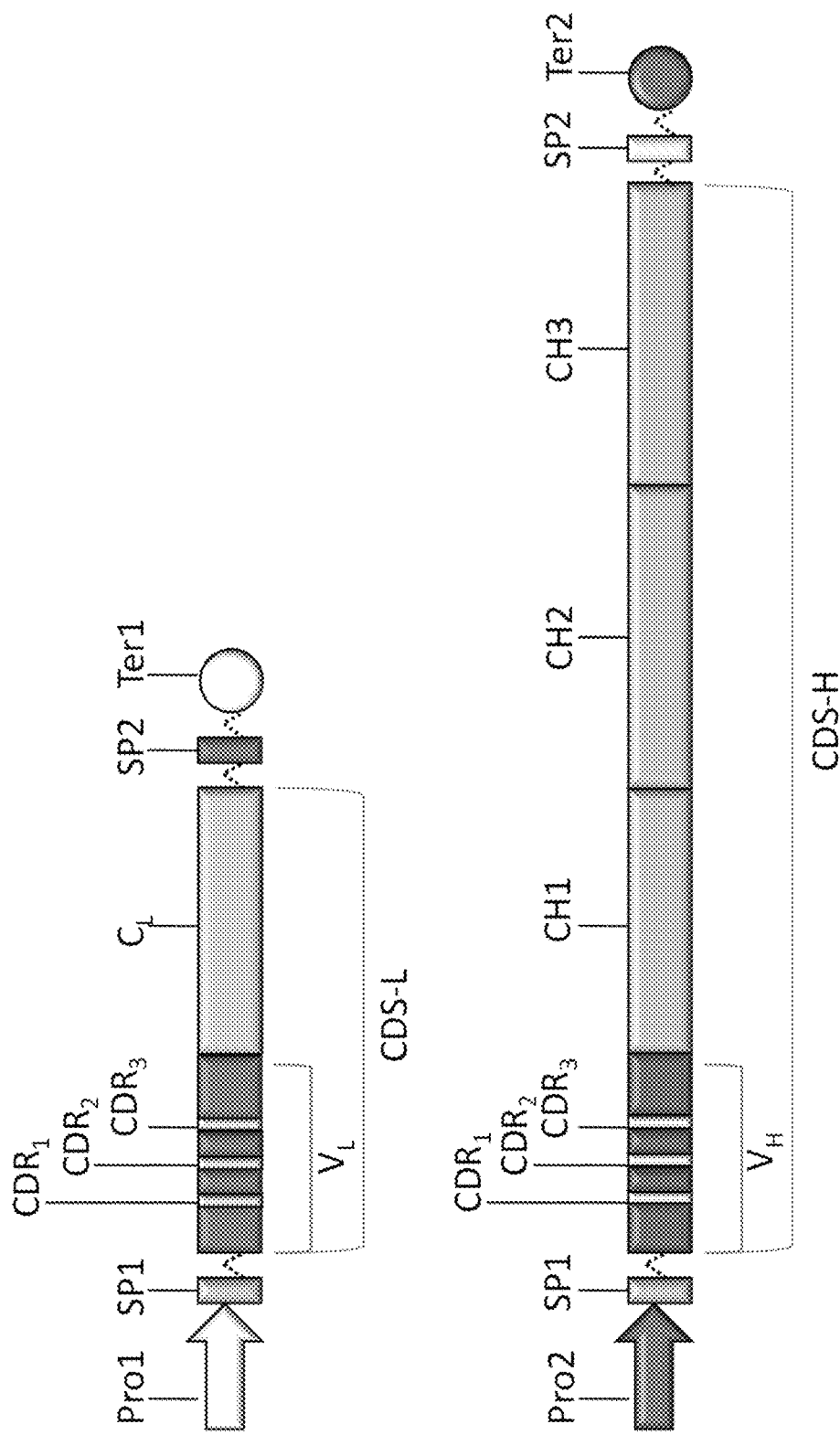
FIG. 13 shows the general scheme of composition of the molecular cassettes for expression in plants of the H and L chains; Legend—Pro½:½ promoter; SP½: sequence of ½ signal peptide; Ter½: ½ terminator; CDS-L/H: sequence coding for the L/H chain; $V_{L/H}$: variable region of the L/H chain; CDR$_{1/2/3}$: hypervariable regions of the heavy and light chain; CL: constant region of the light chain; CH1$_{1/2/3}$: constant regions of the heavy chain.
Figure 14:
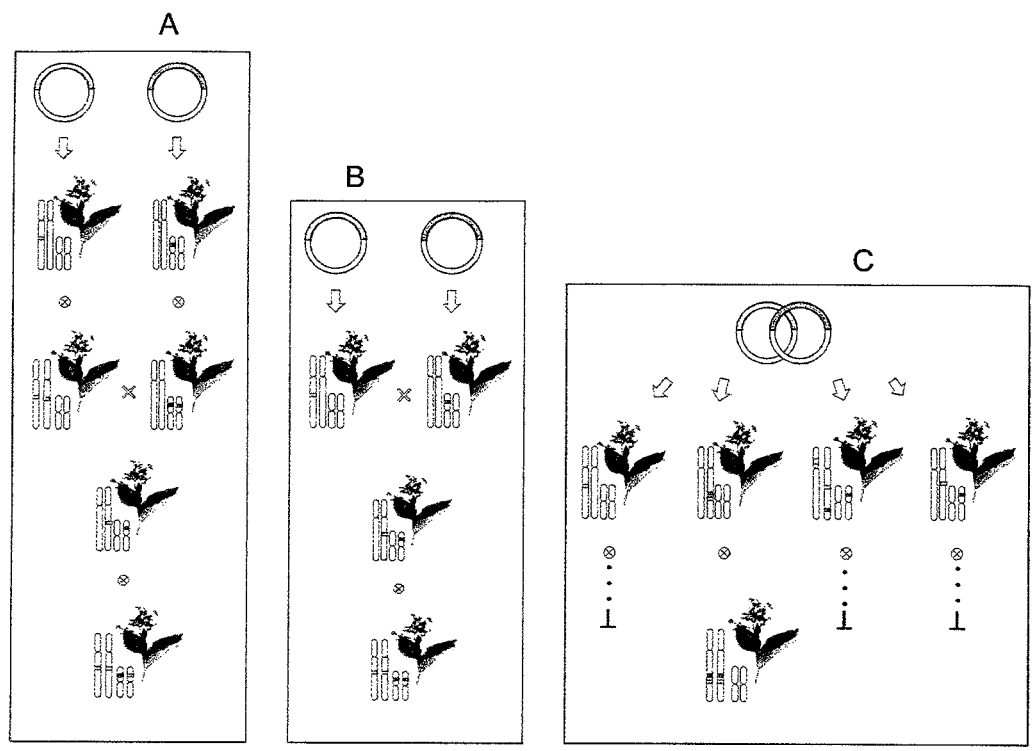
FIG. 14 is a schematic representation of the most commonly used strategies for expression of whole antibodies in plants. A: disjointed use of molecular vectors for the separate expression of H and L chains followed by hybridization of homozygous lines for transgenes; B: variant of A in which hybridization is carried out at the level of primary transformants; C: jointed use of molecular vectors for the combined expression of H and L chains in primary transformants (co-transformation)
Figure 15:
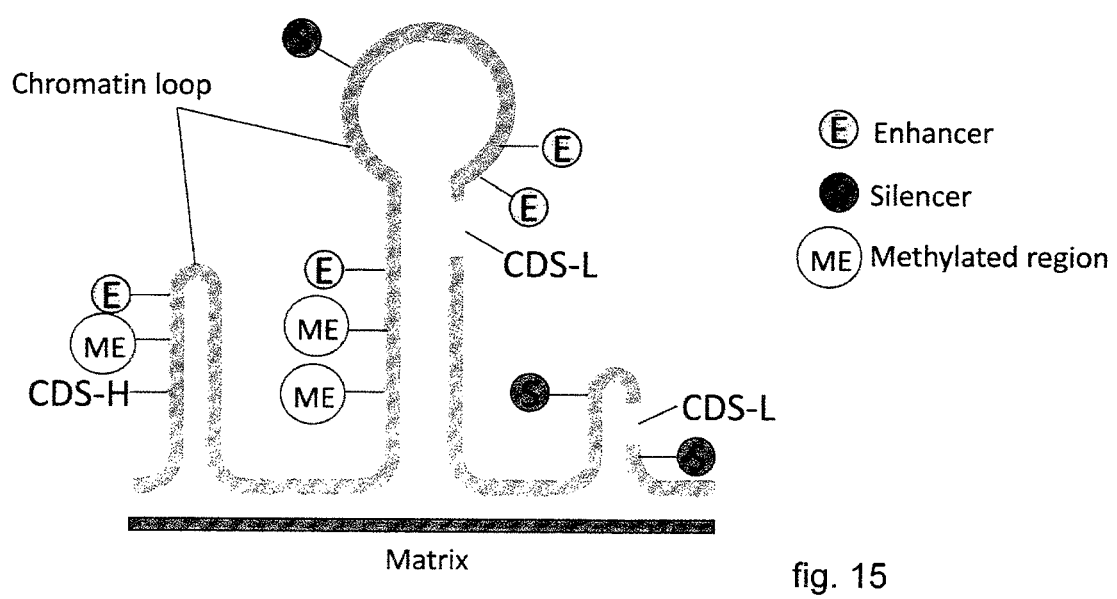
FIG. 15 schematically shows an example of position effect: the transgenes carrying the information for the synthesis of the L and H chains are differently expressed due to the interference generated by enhancer elements (E), silencers (S) and regions containing methylated DNA (ME).

To determine the most probable proteolytic cleavage site of the PSGluB-4/L and PSGluB-4/H complexes, the SignalP 3.0 software was used (http://www.cbs.dtu.dk/services/SignalP). This site was located exactly between PS and L/H (PS-L: MATIAFSRLSIYFCVLLLCHGSMA//QIVLSQ-SPAI . . . ; PS-H: MATIAFSRLSIYFCVLLLCHGSMA//QVQLQQPGAE . . . ) (FIG. 1). The amino acid sequences of the light (L) and heavy (H) chains of the Rituximab antibody were inferred from U.S. Pat. No. A-5,736,137. The nucleotide sequences encoding the above chains, as well as PSGluB-4, were artificially synthesized by choosing the individual codons (codon context method) and this in view of a high expression in rice; these sequences, corresponding to SEQ ID NO: 8 (light chain of Rituximab) and SEQ ID NO: 9 (heavy chain of Rituximab), are therefore different from those reported in the above patent but nevertheless perfectly synonymous therewith (FIG. 3).

The nucleotide sequences for L and H are reported in SEQ ID NO: 5 and SEQ ID NO: 6, respectively.

The polyadenylation signal used in both expression cassettes was NOS ter, that is, the terminator of the gene encoding nopaline synthase of *Agrobacterium tumefaciens*. The sequence of NOS ter is indicated in SEQ ID NO: 7.

The expression cassette of each light (L) and heavy (H) chain of the antibody was then constituted through the consecutive joining of the above elements, exploiting specific restriction sites.

The cassettes were introduced in the final expression vector, which is therefore a single vector, called pTRS, developed by the Applicant and already equipped, inside the T-DNA, with the PMI (phospho-mannose isomerase) selection cassette. After verification of all the sequences used in the construction of the final expression vector, called pTRS_Rituximab (FIG. 2), whose entire sequence is indicated in SEQ ID NO: 1, it was introduced by electroporation into *Agrobacterium tumefaciens*, strain EHA 105. After suitable controls, the engineered strain was used for the transformation of rice embryogenic calli (*Oryza sativa* ssp. *japonica*, variety CR W3).

The entire procedure of transformation and regeneration of seedlings on a selective substrate took place regularly. One hundred and eighty primary transformants were obtained; once they reached maturity, the seed of each of them was collected to be used in subsequent analyses concerning both the verification of the presence of the antibody and its level of expression, and also the selection for the identification of the best expressors, to be used for the creation of progeny and the establishment of the production line.

Like the primary transformants, the progeny also developed normally and produced seed containing the recombinant antibody of interest.

The presence of the antibody in the transformed rice flour was demonstrated by DAS-ELISA (FIG. 5). The same immunological assay was used for the selection of primary transformants characterized by single T-DNA insertion events on which to found the development of highly productive homozygous lines.

Using the seed produced by the transformed plants, Applicant developed protocols for processing the seed itself, obtaining raw protein extracts and the extraction/purification of the recombinant antibody. The latter procedure is essentially based on a capturing step with affinity chromatography on protein A and a final polishing step by gel-filtration. Processing the seed (dehulling and whitening) proved to be extremely useful in removing most of the contaminating proteins; Rituximab extracted from processed and purified rice flour using protein A showed a high degree of purity, more than 95% (FIG. 7).

In SDS-PAGE performed under denaturing and non-reducing conditions, the purified protein showed a mobility wholly comparable to the commercial standard Rituxan® (Genentech-Roche), with an apparent molecular weight of about 150 kDa; this weight corresponds to that expected for the whole antibody consisting of two light chains (about 25 kDa each) and two heavy chains (about 50 kDa each).

The same purified sample subjected to gel filtration showed two elution peaks (FIG. 8); a first minority peak, containing the dimer of the antibody molecule, and a second one, clearly dominant, corresponding to the monomer, correctly assembled, and having a retention volume superimposable to that of commercial Rituximab (Rituxan®) (FIG. 9).

Further biochemical analyses based on peptide mapping in MALDI-TOF aimed to test the integrity of the antibody produced in rice endosperm and the full identity of the amino acid sequence between the latter and its commercial counterpart. Repeated MALDI-MS analyses on tryptic digests of the purified antibody from rice flour also confirmed the absence, on both chains, of the signal peptide and the presence on the heavy chain of a single N-glycosylation site at the level of Asn 325, as expected. This site is occupied and the glycosylation profile is attributable to the paucimannose type with a fucosylated core with and without a xylose residue (FIG. 10).

The purified recombinant antibody obtained according to the present description proved to have a functional bioequivalence with respect to its commercial counterpart: actually, the sample tested demonstrated to recognize the CD20 epitope and to compete effectively with Rituxan®; moreover, the same co-localization of the epitope/antibody bond was observed. In fact, in the in vitro tests (example 9) on live and non-aggregated MEC-1 cells (FIG. 11*a*, section A), FACS analysis indicated that Rituxan® recognizes 98.91% of MEC-1 cells (FIG. 11a, section B), while the one produced in rice seed (RTX PBS) is 98.33% (FIG. 11a, section C). This data, together with the mean fluorescence intensity (FIG. 11b), shows that the two antibodies have the same ability to bind the CD20 antigen. In the competition assay conducted on MEC-1 cells in the presence of Rituxan® or an unrelated antibody but able to recognize the CD52 epitope close to CD20 (Campath), it was also possible to show that the Rituxan® antibody and RTX PBS compete specifically for the same site (FIG. 12).

From the immuno-fluorescence analysis conducted on MEC-1 cells incubated in the same saturating conditions used to perform the FACS analysis, it was also possible to ascertain that the rice-derived RTX PBS antibody has the same localization as the antigen/antibody bond of Rituxan®: the concentration of the CD20 antigen was in fact highlighted in a single membrane region thanks to the co-localization of the signals supplied by the fluoresceinated anti-CD20 antibodies (Rituxan®, RTX PBS) compared to FastDil, used to mark the membranes (Example 9); the result appeared even more evident where direct immunofluorescence was observed by using RTX PBS conjugated with FITC.

EXAMPLES

Example 1: Production of the Final Expression Vector pTRS_Rituximab

A procedure is provided below, by way of example, able to produce an expression vector which can be used in the genetic transformation of rice for the endosperm-specific expression of the Rituximab antibody according to possible embodiments described here. Similar procedures can be used to obtain other antibodies or to make variants of the construct characterized by the presence of other endosperm-specific promoters and/or sequences for targeting into the endoplasmic reticulum and/or terminators.

Artificial Synthesis of Coding Sequences

Each chain constituting the Rituximab antibody (light and heavy, abbreviated L and H, respectively) was expressed in rice through a nucleotide sequence optimized at the codon level (codon context method); both sequences encoding the light (L) and heavy (H) polypeptide chains were artificially synthesized to be inserted into the expression cassettes. Based on the molecular biology steps planned in silico, the artificially synthesized segment was found to contain: a part of the GluB-4 promoter (starting from nucleotide position 906, for a total of 525 bp), a leader sequence (5'-UTR) of 70 bp and the entire sequence encoding the polypeptide chain considered (714 bp for light chain L, 1428 bp for heavy chain H). To facilitate cloning operations in plasmid, the restriction sites Spe I and Sac I were put at terminals 5' and 3', respectively. Both programmed fragments, called light chain and heavy chain of 1315 and 2029 bp respectively, once synthesized, were cloned into a specific vector.

Production of Molecular Expression Cassettes

The intermediate vector pUC18 (ThermoScientific) was used to make the expression cassettes of each Rituximab chain. More specifically, the vector pUC18//GluB-4::NOS, was used; this vector was previously produced by the Applicant in such a way to supply both the GluB-4 rice promoter (GeneBank Acc. No. AY427571), and the nopaline synthase terminator of Agrobacterium tumefaciens (NOS, GeneBank Acc. No AF485783). The insertion of the light chain fragment into pUC18//GluB-4::NOS took place by means of an oriented cloning, exploiting the restriction sites Spe I and Sac I.

Figure 4A:
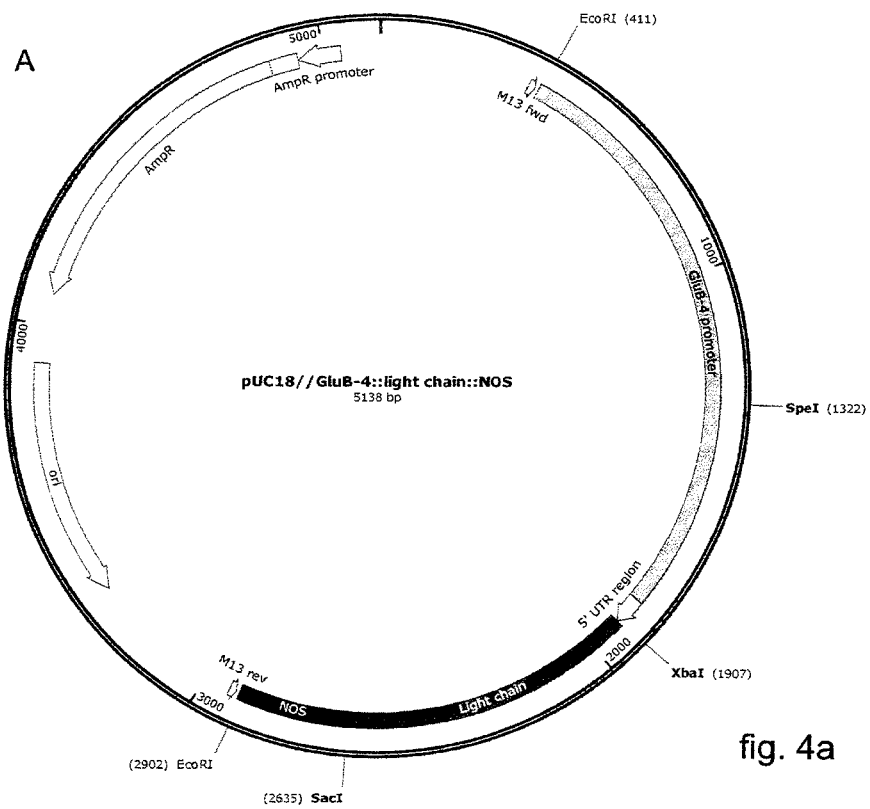
FIGS. 4a and 4b show the map of the vectors pUC18//GluB-4::light chain::NOS (section A) and pUC18//(PmeI)GluB-4::heavy chain::NOS(PmeI) (section B) containing the expression cassettes for the light chain and heavy chain of Rituximab.
Figure 4B:
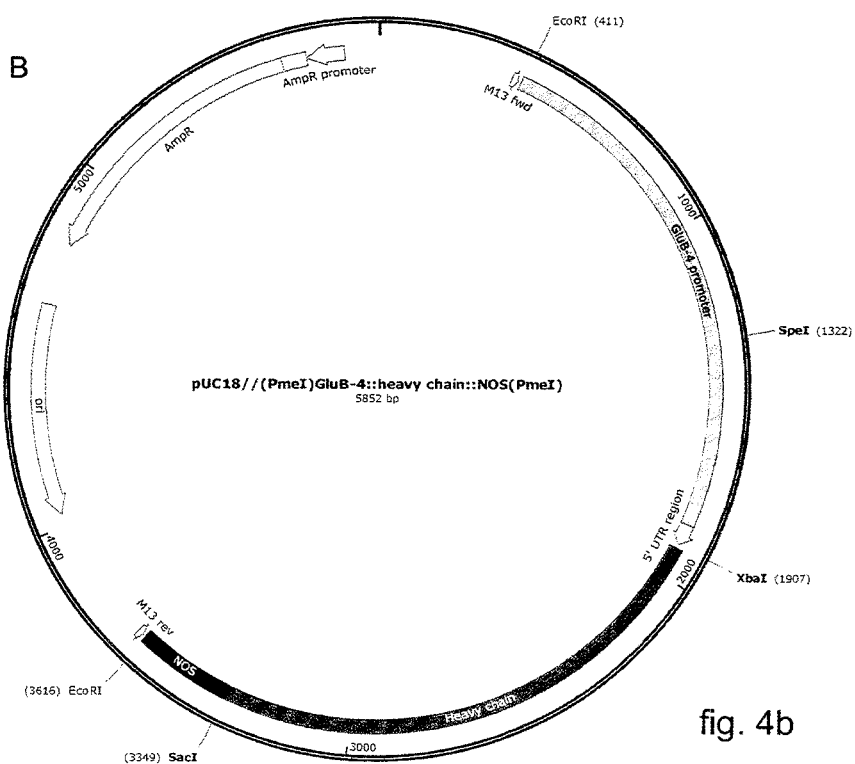

The insertion of the heavy chain fragment into a second pUC18//GluB-4::NOS was equally carried out by oriented cloning, exploiting the restriction sites Spe I and Sac I; in this case, however, before this last step, it was necessary to carry out a work to modify the vector pUC18//GluB-4::NOS. In particular, in order to facilitate the transfer of the expression cassette in the final vector (see next paragraph), it was necessary to replace the restriction site Eco RI, present both at the terminal 5' of the GluB-4 promoter, and also at the 3' of the NOS terminator, with the site Pme I. This replacement was performed by PCR with a specific linker design that allowed to obtain, through some intermediate molecular biology steps and control by sequencing, the vector pUC18//(Pme I) GluB-4::NOS(Pme I). This last vector was then used to insert the heavy chain fragment. In this way, the two vectors were constructed, carrying the expression cassettes relating to each light and heavy Rituximab chain, namely: pUC18//GluB-4::light chain::NOS and pUC18//(Pme I) GluB-4::heavy chain::NOS(Pme I) (FIG. 4).

Construction of the Final Expression Vector

Figure 2:
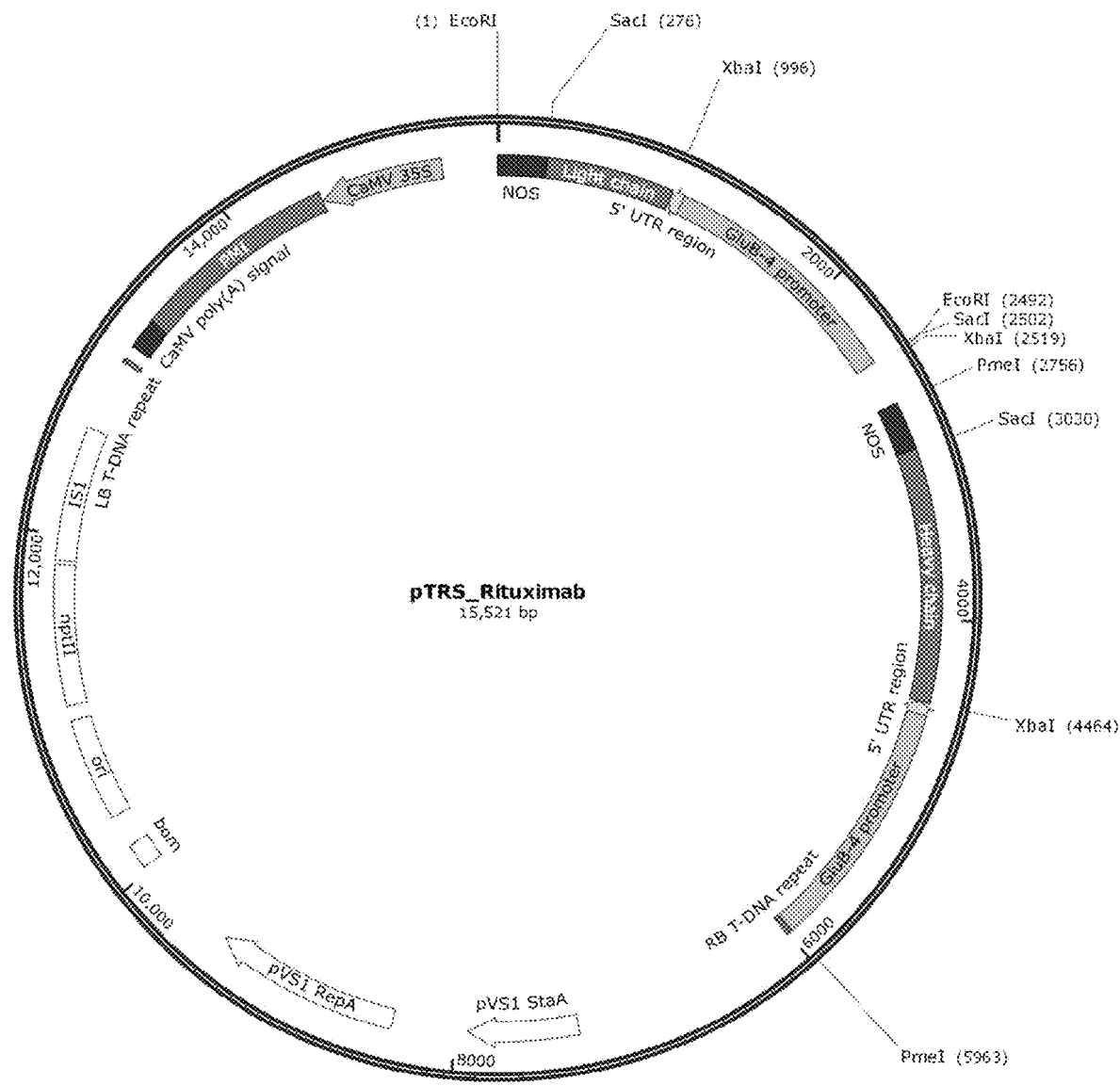
FIG. 2 is a map of the final pTRS_Rituximab expression vector used for endosperm-specific production of the Rituximab antibody.

To this purpose, pTRS, a plasmid vector developed by the Applicant, was used, characterized by the following functional elements fundamental for the molecular manipulation of the expression cassettes: 1. gene npt II (present at vector backbone level), which confers resistance to kanamycin in the selection of transformed bacterial strains; 2. PMI gene (located inside the T-DNA), encoding for the phospho-mannose isomerase enzyme, to be used as a positive selection agent in the early identification of the transformed plants. The pTRS vector was used as an acceptor of both expression cassettes relating to the light and heavy chain of Rituximab. The cloning of the two cassettes took place sequentially, through the restriction sites Eco RI and Pme I, respectively. The final expression vector (FIG. 2) was then subjected to sequence verifications before being inserted by electroporation in Agrobacterium tumefaciens, strain EHA 105. The engineered strain of Agrobacterium was ultimately used for the transformation of Oryza sativa ssp. japonica, var. CR W3.

Example 2: Genetic Transformation of Oryza sativa by Agrobacterium tumefaciens

For the genetic transformation of rice the Hiei et al. protocol (1994) was used, modified by Hoge (Rice Research Group, Institute of Plant Science, Leiden University) and Guiderdoni (Biotrop program, Cirad, Montpellier, France) until the transformed calli were obtained. For the subsequent selection step of the transformed plant tissues, the Datta and Datta protocol (2006) was applied, which exploits as a marker system the phospho-mannose isomerase enzyme in association with increasing concentrations of mannose in the culture medium. The main steps performed are briefly described below.

Preparation and Development of Embryogenic Calli from Rice Scutellum

The transformation of rice took place on embryogenic calli derived from scutellum. To induce the proliferation of calli from scutellum tissue, the following operating protocol was used:

dehulling (mechanical removal of the glumes) of 500 rice seeds was carried out;

in order to eliminate potential pathogens and contaminating saprophytes, dehulled seeds were disinfected;

the first disinfection treatment provided the dehulled seeds to stay for 2 minutes in a 70% ethanol solution;

subsequently, the dehulled seeds were transferred to a 5% sodium hypochlorite solution with 2 drops of Tween-20 detergent and kept there in slow stirring for 30 min;

to eliminate all traces of sodium hypochlorite, three washes were carried out with sterile $H_2O$ for a duration of 15 min each;

after the last washing, the dehulled seeds were dried on sterile tissue paper;

on the surface of the callus-induction medium (CIM), dispensed in the volume of 25 mL inside Petri dishes (Ø 90 mm), 12 dehulled seeds per plate were positioned;

the plates obtained in this way were incubated in the dark, at a temperature of 28° C. for 21 days; after 1 week of induction, the endosperm and the radicle were eliminated to promote the development of the callus coming from the scutellum (the scutellum is recognized by its compact mass, partly included in the yellow colored endosperm);

after 3 weeks of induction, the callus was transferred onto a renewed CIM, followed by the fragmentation of the callus mass without the use of scalpels, following the fraction lines naturally present on the callus;

sub-culture continued for 10 days in order to develop the embryogenic callus and make it suitable for transformation.

Co-Cultivation of the Calli with *A. tumefaciens*

To obtain sufficient quantities of *A. tumefaciens* for transformation, the colony a, carrying the binary expression system, was grown in LB medium; the bacterial suspension was then plated in Petri dishes containing agar-kanamycin LB;

After 3 days of culture at 30° C., the bacterial patina was removed and suspended in the co-cultivation medium liquid (CCML), until obtaining an O.D. 600 of about 1.0, corresponding to 3-5 $10^9$ cells/mL;

the best calli, that are those with a diameter of about 2 mm, compact and whitish in color, were transferred to a Petri dish containing 35 mL of bacterial suspension and left immersed for 15 min;

then the calli were dried using sterile tissue paper;

a maximum number of 20 calli per high-edge Petri dish (Sarstedt) containing the co-cultivation medium solid (CCMS) was disposed;

the calli were then incubated in the dark, at a temperature of 25° C. for 3 days.

Selection of the Transformed Calli Using the PMI System

After the co-cultivation of the embryogenic calli of rice with *agrobacterium* was carried out, the transformed tissues were selected, exploiting the conversion capacity of the mannose-6-phosphate in fructose-6-phosphate acquired with the insertion of the gene encoding the phospho-mannose isomerase of *E. coli*. The procedure used for this purpose was as follows:

transfer of the calli arriving from co-cultivation to a mannose-free substrate containing 3% sucrose (SMI); incubation for 1 week in the dark at a temperature of 28° C.;

transfer of the calli to SMII selection substrate containing 2% sucrose and 1.5% mannose and incubation in the dark for 2 weeks at a temperature of 28° C.;

transfer of the calli to SMII selection substrate containing 1% sucrose and 2% mannose and incubation in the dark for 2 weeks at a temperature of 28° C.;

transfer of the calli to PRM (Pre-Regeneration Medium) containing 0.5% sucrose and 2.5% mannose and incubation in the dark for 2 weeks at a temperature of 28° C.

Regeneration of Rice Seedlings from Transformed Calli non-browned calli were transferred to high-edge Petri dishes containing the mannose-free Regeneration Medium (RM);

after 48 hours, the dishes containing the selected calli were exposed to light;

when the seedlings were found to be large enough to be separated from the callus (>3 cm in height), they were transferred to culture tubes containing the rooting medium (rm);

the sub-culture inside tubes continued for about 3 weeks, always at 28° C. in the light;

at the end of the regenerative process, the plants were transferred to peat and grown in the greenhouse.

The following tables show the composition of the various substrates used in the protocol of genetic transformation of rice.

| Substrate composition | CIM | CCML | CCMS | SMI | SMII 2 + 1.5 | SMII 1 + 2 | PRM 0.5 + 2.5 | RM | rm |
|---|---|---|---|---|---|---|---|---|---|
| N6 macroelements I (mL) | 60 | | | | 60 | 60 | 60 | 60 | |
| N6 macroelements II (mL) | 60 | | | | 60 | 60 | 60 | 60 | |
| MS FeNaEDTA (mL) | 10 | | | | 10 | 10 | 10 | 10 | |
| B5 vitamins (mL) | 10 | | | | 10 | 10 | 10 | 10 | |
| B5 microelements (mL) | 1 | | | | 1 | 1 | 1 | 1 | |
| $R_A$ (mL) | | 26 | 26 | 26 | | | | | |
| $R_B$ (mL) | | 26 | 26 | 26 | | | | | |
| $R_C$ (mL) | | 26 | 26 | 26 | | | | | |
| MS salts (mL) | | | | | | | | | 100 |
| Proline (mg) | 600 | | | | 600 | 600 | 600 | 600 | |
| Glutamine (mg) | 600 | | | | 600 | 600 | 600 | 600 | |
| Glycine (mg) | | | | | | | | | 2 |
| CEH (Hydrolyzed casein) (mg) | 300 | | | | 300 | 300 | 300 | 300 | |
| MES (mg) | 500 | 500 | 500 | 500 | 500 | 500 | 500 | 500 | 500 |
| Acetosyringone (mM) | | 0.1 | 0.1 | | | | | | |
| Glucose (g) | | 10 | 10 | | | | | | |
| Sucrose (g) | 30 | | | 30 | 20 | 10 | 6 | 30 | 50 |
| Mannose (g) | | | | | 15 | 20 | 25 | | |
| 2,4-D (mg) | 2.5 | 2.5 | 2.5 | 2.5 | 2.5 | 2.5 | | | |
| ABA (mg) | | | | | | | 5 | | |
| BAP (mg) | | | | | | | 2 | 3 | |
| NAA (mg) | | | | | | | 1 | 0.5 | |

-continued

| Substrate composition | CIM | CCML | CCMS | SMI | SMII 2 + 1.5 | SMII 1 + 2 | PRM 0.5 + 2.5 | RM | rm |
|---|---|---|---|---|---|---|---|---|---|
| Nicotine acid (mg) | | | | | | | | | 0.5 |
| Thiamine (mg) | | 1 | 1 | 1 | | | | | 0.1 |
| Pyridoxine (mg) | | | | | | | | | 0.5 |
| Inositol (mg) | | | | | | | | | 100 |
| SPI Agarose (g) | | | 7 | 7 | 7 | 7 | | | |
| Phytagel (g) | 2.5 | | | | | | 4.5 | 4.5 | 2.5 |
| Cetotaxime (mg) | | | | 400 | 400 | 400 | 250 | 50 | |
| H2O | q.b. a 1 L | q.b. a 1 L | q.b. a 1 L | q.b. a 1 L | q.b. a 1 L | q.b. a 1 L | q.b. a 1 L | q.b. a 1 L | q.b. a 1 L |

Legend. CIM: Callus induction medium; CCML: co-cultivation medium liquid; CCMS: co-cultivation medium solid; PSM: pre-selection medium; SMI: selection medium I; SMII: selection medium II; PRM: pre-regeneration medium; RM: regeneration medium; rm: rooting medium.

| N6 macroelements II | Dose per L |
|---|---|
| $CaCl_2 2H_2O$ | 3.32 g |

| N6 macroelements I | Dose per L |
|---|---|
| $KNO_3$ | 56.60 g |
| $(NH_4)SO_4$ | 9.26 g |
| $KH_2PO_4$ | 8.00 g |
| $MgSO_4 7H_2O$ | 3.70 g |

| B5 microelements | Dose per L |
|---|---|
| $MnSO_4 H_2O$ | 10 g |
| KI | 0.75 g |
| $H_3BO_3$ | 3 g |
| $ZnSO_4 7H_2O$ | 2 g |
| $CuSO_4$ | 0.025 g |
| $Na_2MoO_4 2H_2O$ | 0.25 g |
| $CoCl_2 6H_2O$ | 0.025 g |

| B5 Vitamins | Dose per L |
|---|---|
| Inositolo | 10 g |
| Tiamina-HCl | 1 g |
| Acido nicotinoco | 0.1 g |
| Pirioxina-HCl | 0.1 g |

| Stock Solution $R_A$ | Dose per L |
|---|---|
| $KNO_3$ | 162 g |

| Stock Solution $R_C$ | Dose per L |
|---|---|
| $CaCl_2 H_2O$ | 6 g |
| $H_3BO_3$ | 114.4 mg |
| $Na_2MoO_4 2H_2O$ | 5.2 mg |
| $FeSO_4 7H_2O$ | 496 mg |
| $Na_2EDTA 2H_2O$ | 668 mg |

| MS FeNaEDTA | Dose per L |
|---|---|
| $FeSO_4 7H_2O$ | 2.784 g |
| $Na_2EDTA 2H_2O$ | 3.724 g |

| MS Salts | Dose per L |
|---|---|
| $MnSO_4 H_2O$ | 16.9 mg |
| $CuSO_4 5H_2O$ | 0.025 mg |
| $ZnSO_4 7H_2O$ | 8.63 mg |
| $CaCl_2 2H_2O$ | 440 mg |
| $KH_2PO_4$ | 170 mg |
| KI | 0.83 mg |
| $NH_4NO_3$ | 1.650 g |
| $KNO_3$ | 1.9 g |
| $NaMoO_4 2H_2O$ | 0.25 mg |
| EDTAFeNa | 40 mg |

-continued

| | |
|---|---|
| $H_3BO_3$ | 6.2 mg |
| $MgSO_4 7H_2O$ | 370 mg |
| $CaCl_2 6H_2O$ | 0.025 mg |

| Stock Solutution $R_B$ | Dose per L |
|---|---|
| $MgSO_4 7H_2O$ | 10 g |
| $(NH_4)_2SO_4$ | 13.2 g |
| $NaH_2PO_4 H_2O$ | 11 g |
| $ZnSO_4 7H_2O$ | 88 mg |
| $MnSO_4 H_2O$ | 80 mg |
| $CuSO_4 5H_2O$ | 8 mg |

Example 3: Extraction of Total Proteins from Rice Flour

The transformed rice seeds were initially dehulled and whitened with Satake TO-92 whitening equipment (Satake Corporation, Japan). The polished seeds were ground with a bench rotor mill (Retsch, Germany), using a 0.5 mm screen; the resulting flour was then homogenized in extraction buffer (50 mM sodium-phosphate, 500 mM NaCl, pH 7.2), with a ratio of buffer volume (mL) and weight of flour (g) equal to 5:1. After incubation at 4° C. under stirring for 1 hour, a centrifugation at 3000×g was performed for 10 minutes. After the supernatant was recovered, the residual pellet was subjected to two further extractions, with the following modifications: the ratio between extraction buffer and flour was 5:1 in the second extraction and 4:1 in the third. Ice incubation was performed for only 10 min; after these steps, a centrifugation at 3000×g for 10 minutes always followed. The three supernatants were then combined to form a single sample used in the purification tests.

Example 4: Das-ELISA for the Detection of the Plant-Derived Rituximab Antibody

The assay was developed and applied to quantitatively track the presence of the antibody in rice seeds. It was used both to validate the presence of the recombinant molecule in batches of transformed biomass, and also in the selection of primary transformants.

A 96-well flat-bottomed polystyrene plate (Costar) was coated with a Goat anti-human IgG (Fc) (Millipore) antibody diluted to a concentration of 0.5 μg/mL in a buffer of 2 mM sodium phosphate and 30 mM sodium chloride, pH 7.2; 100 μL of this solution were dispensed into each well. The coating process was completed in 20 min at room temperature, under stirring.

After removal of the coating solution, the plate was blocked for 20 min with 250 μL/well of a 1% BSA (Sigma) solution in PBS, added with 0.01% sodium azide.

After removal of the blocking solution, 50 µL of sample was sown in each well, appropriately diluted in PBS, 1% BSA, 0.1% Tween-20 (Sigma), freshly prepared. The samples were incubated for 20 min at 37° C. under stirring.

After the samples were removed, the wells were washed three times with 300 µL PBS, 0.1% Tween-20, freshly prepared.

50 µL of anti-human IgG (Fc) conjugated with HRP (Millipore) diluted to a concentration of 0.25 µg/mL in PBS, 1% BSA, 0.1% Tween-20 was added to each well. A 20 min incubation followed at 37° C. under stirring.

After removal of the conjugated antibody solution, the wells were washed four times with 300 µL PBS, 0.1% Tween-20, freshly prepared.

100 µL TMB (KPL) was added to each well. The development took place in about 5 min at 37° C., under stirring.

The development was stopped with 100 µL/well of 1 M hydrochloric acid. The sample absorbance was read at a wavelength of 450 nm.

To construct the reference curve used in the assay, the drug Rituximab (Rituxan®, Genentech-Roche) was used; the concentration range used was 0.3125-5 pg/µL. The assay was then able to give a linear response for concentrations of Rituximab ranging from 2 to 40 ng/mL. For a good evaluation of the antibody content in the primary transformants, a 1:600 dilution of the total protein extracts obtained from the processed seed flour was used.

Example 5: Analyses of 180 Primary Transformants for the Identification of the Rituximab Antibody To detect the presence of Rituximab antibody in the samples of transformed rice, a total protein extraction of 40 seeds produced by each primary transformant was carried out, according to the following protocol:
milling of each sample with a Retsch MM 200 digital mill for 1 minute at a speed of 15 Hz;
recovery of the flour in an Eppendorf-type test tube marked with a specific identification code;
sampling of 70 mg of the flour obtained;
homogenization of the flour with 1 mL of extraction buffer in an Eppendorf-type test tube marked with a specific identification code;
transfer of the suspension to a marked Falcon tube containing 7 mL of extraction buffer;
incubation of the tubes for 1 h in ice under stirring;
transfer of 1 mL of extract into a marked Eppendorf test tube and centrifugation at 16,000×g, at 4° C. for 40 minutes;
recovery of the supernatant and its transfer into a new marked Eppendorf test tube;
storage of the remaining extract at −20° C.

Figure 5:
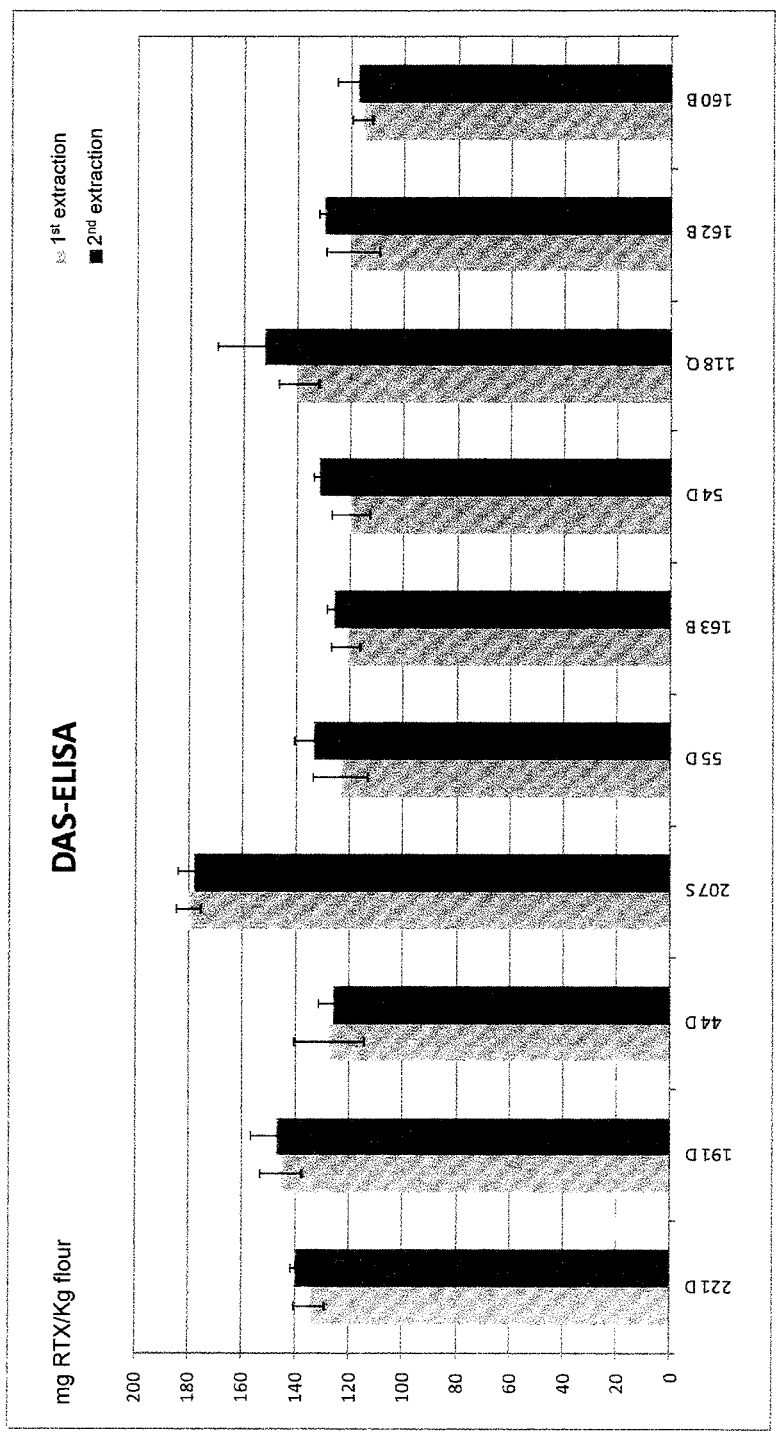
FIG. 5 shows the data obtained in DAS-ELISA for the detection of Rituximab in two independent protein extracts prepared from flours of 10 rice primary transformants.

This method differs from the one reported in Example 3 by the presence of a single extraction intervention; by virtue of its greater simplicity, it lends itself extremely well to the analysis of numerous samples, in particular of segregating progenies derived by self-fertilization from primary transformants. Although the procedure entails a partial extraction of the antibody, it allows to evaluate with great accuracy the entity of gene silencing phenomena that can be attributed to the presence of repeated sequences. Immunological analysis (DAS-ELISA, as in Example 4) has shown that only in 1 case out of 180 (0.56%) was it not possible to detect the presence of the recombinant antibody; this shows that the invention solves the problems and limitations of the state of the art very effectively. For a greater solidity of the data, the immunological analysis was repeated on a second extract of each sample with the same result; by way of example, FIG. 5 shows the values obtained in duplicate on the protein extracts relating to 10 primary transformants.

After repeated self-fertilization and selection of homozygous lines, the Rituximab content was determined by DAS-ELISA (as in Example 4) in extracts obtained with the complete procedure described in Example 3. In 3 independent lines characterized by single insertion events of T-DNA, the Rituximab content was as follows: 0.950 g/kg, 1.072 g/kg, 0.923 g/kg. These values demonstrate how the invention allows not only to simplify the transformation and selection procedure of the transformed lines in the absence of silencing phenomena but also to obtain antibody yields absolutely suitable for industrial applications.

Example 6: Purification of the Plant-Derived Rituximab Antibody

For the purification of the Rituximab antibody, a protocol based on protein A was applied; all the chromatographic steps were performed with the AktaPurifier UPC-100 (GE Healthcare) chromatograph.

Figure 6:
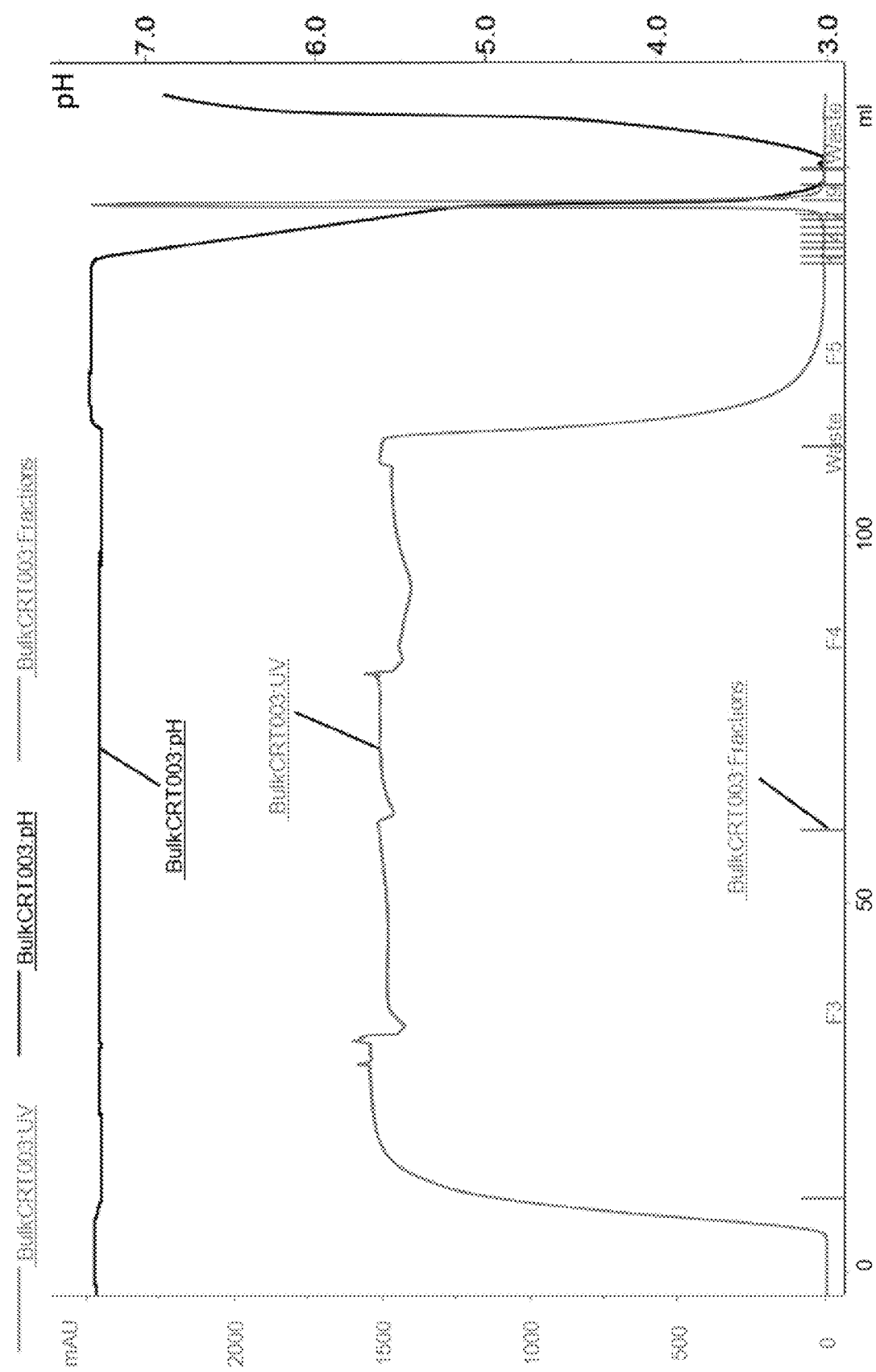
FIG. 6 shows the graphs of UV absorbance and pH relating to an affinity chromatographic run on protein A for the purification of a batch of Rituximab from a protein extract of transformed rice. The segments depicted on the x-axis highlight the collected fractions (from 1 to 11), in particular those corresponding to the peak containing the antibody molecule (fractions 8 and 9)

Prior to purification, the supernatant obtained from the extraction was filtered through Polycap 36 HD cartridge (Whatman), having a porosity of 1 µm. The filtrate was in turn ultra-filtered with a QX-Stand tangential system (GE Healthcare), equipped with a UFP-50-C-4MA cartridge, until 1/10 of the original volume was reached. The retentate was then re-filtered using a 25 mm GD/XP poly-ethersulfone cartridge with 0.45 µm porosity (Whatman). It was then loaded in the Protein A Sepharose FF (GE Healthcare) column; after loading, a wash was carried out in PBS, pH 7.4. The elution was then performed in citrate buffer (50 mM Na-citrate, pH 3.0) with fractional collection of the peak (FIG. 6). The collected fractions were neutralized with 3 M Tris-HCl buffer, pH 8.8, and stabilized for storage with 0.4 M arginine, pH 8.0. The purified sample thus obtained was used both for a biochemical characterization of the antibody molecule (study of the structure of the H and L chains), and also for an in vitro pharmacological test to recognize the antigen.

Figure 7A:
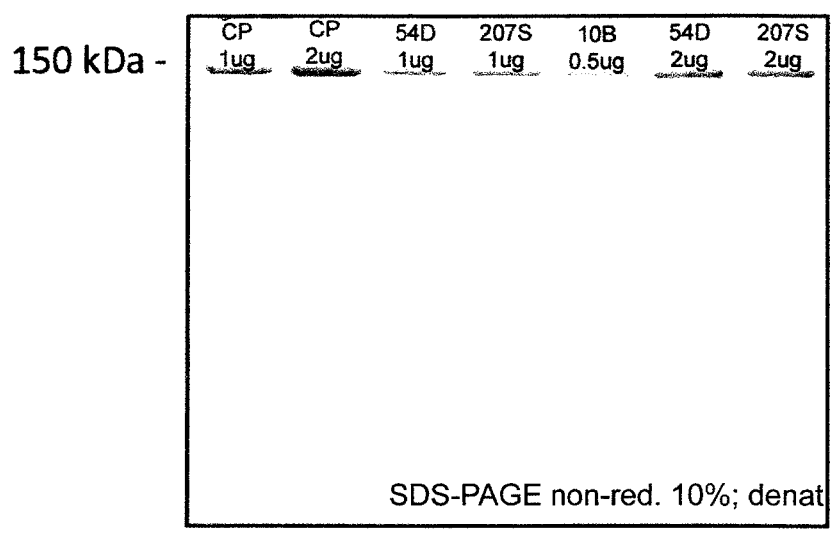
FIG. 7a. shows the SDS-PAGE performed under denaturing and non-reducing conditions on the chromatographic eluate obtained following the capture of the antibody by protein A, for 3 lines of transformed rice (54D, 207S and 10B). Different quantities of protein were loaded (0.5-1-2 µg) using Rituxan® (Genentech-Roche) as a positive control (CP)
Figure 7B:
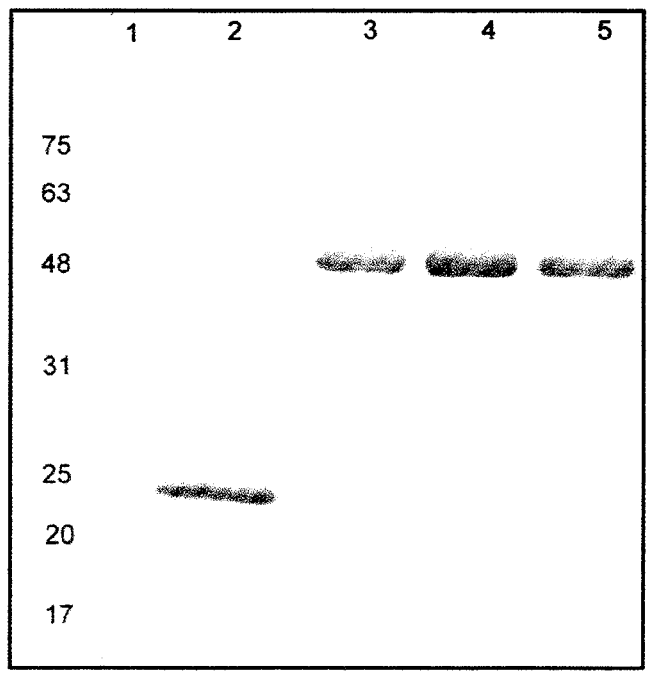
FIG. 7b. shows the SDS-PAGE of fractions deriving from gel filtration; the samples were neutralized, diluted to a final concentration of 2% SDS, 5% beta-mercaptoethanol and denatured at 95° C. for 5 min. Lane 1: molecular marker (Sharpmass VII, Euroclone); 2: fraction containing the light chain; 3-5: fractions containing the heavy antibody chain.
Figure 8:
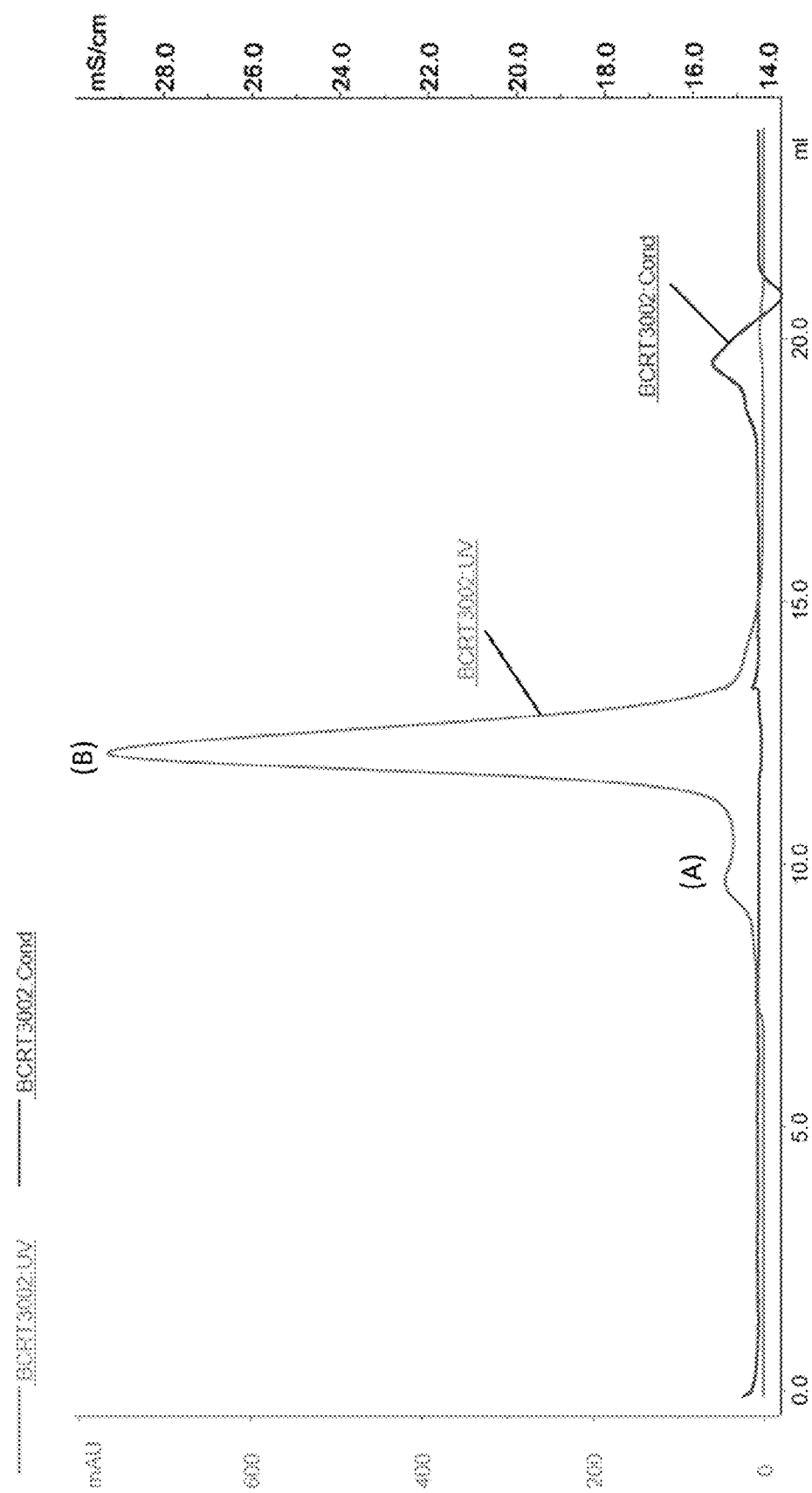
FIG. 8 shows the chromatographic graphs of UV absorbance and conductance relating to a gel filtration performed by isocratic elution with PBS of 4.2 mg of Rituximab previously purified with protein A from rice flour. The two elution peaks are shown, corresponding to the dimer (A) and to the monomer (B) of the antibody molecule.
Figure 9:
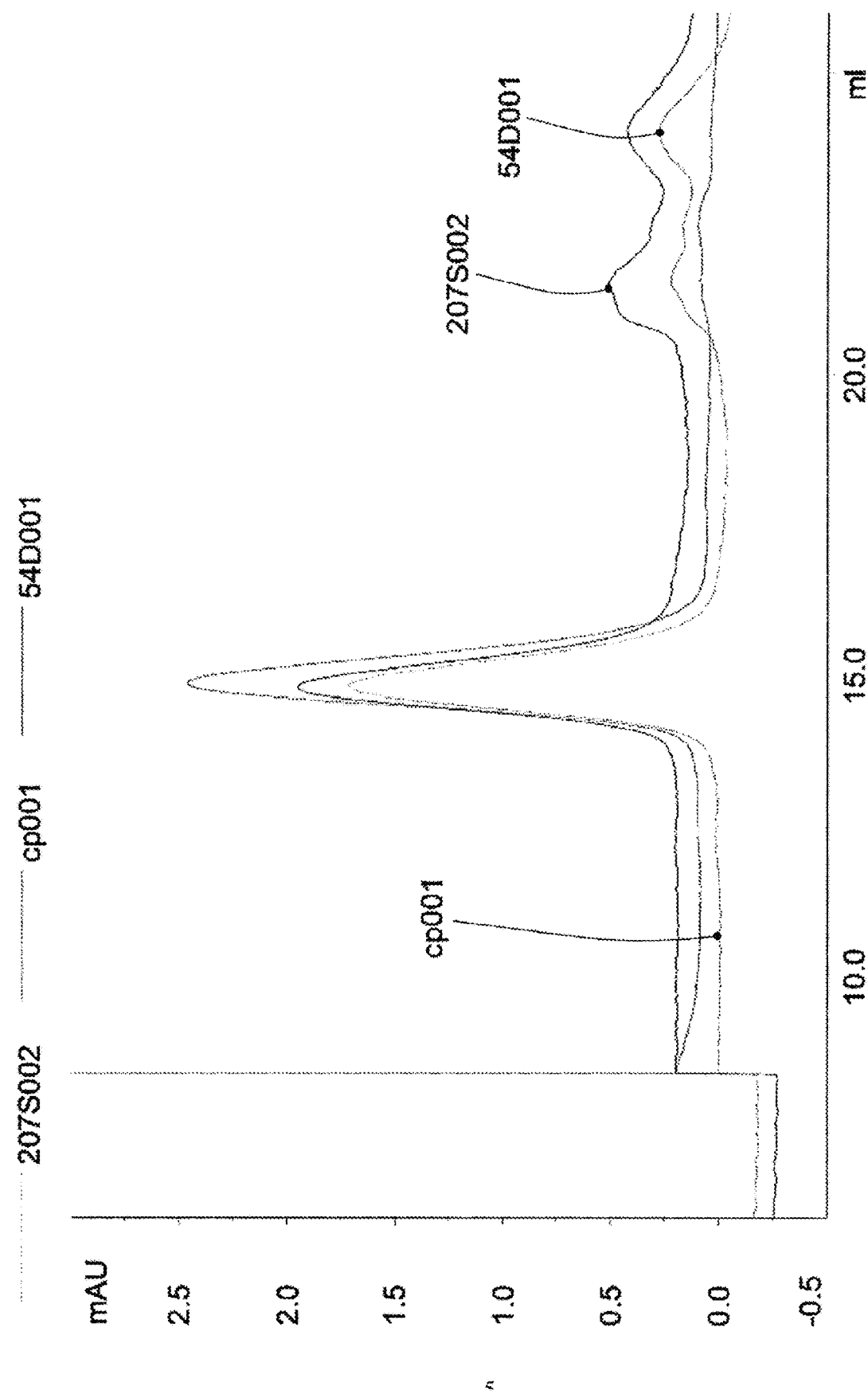
FIG. 9 compares the UV chromatographic graphs of three different gel filtration runs performed on two samples of purified Rituximab from two lines of transformed rice (207S and 54D) and on a Rituxan® sample used as a positive control (cp)

Example 7: Preparatory Filtration Gel for In Vitro Pharmacological Test to Recognize the Antigen A batch of Rituximab produced in endosperm of transgenic rice was purified by chromatography on protein A (see Example 6) obtaining a preparation with a degree of purity higher than 95% on the total protein (FIG. 7); 250 µL of the preparation, having a protein concentration of 17 mg/mL, were loaded into the column by gel filtration Superdex 200 10/300 GL (GE Healthcare) and eluted with PBS buffer at a flow of 0.5 mL/min. The gel filtration eluate was collected in fractions; the plant-derived antibody molecule showed to elute constantly in 2 peaks (FIG. 8). The first peak, smaller, is positioned at a retention volume of 9.5 mL, the second, much larger, is close to a retention volume of 12.1 mL. The first peak contains the antibody dimer; the second peak instead consists of the correctly assembled monomer; to prove this there is the perfect overlap of the peaks and thus of the retention volume recorded for the plant-derived antibody and the commercial Rituximab (Rituxan®, Genentech-Roche) (FIG. 9).

500 µL of the elution fraction containing the monomer (called RTX PBS) were used for the cytofluorimetry experiment, intended to confirm the equivalence of Rituximab produced in rice compared to the commercial counterpart Rituxan® in recognizing the CD20 epitope (Example 9).

Example 8: Biochemical Analysis of Polypeptidic L and H Chains of Rituximab Produced in Rice Endosperm by MALDI-MS A purified Rituximab sample derived from rice, subjected to final gel filtration (Example 7), was subjected to reduction with DTT, alkylation with iodoacetamide and desalting by RP-HPLC.

The fraction collected manually by HPLC was concentrated and then subjected to hydrolysis with trypsin; an aliquot of the peptide mixture thus produced was subjected to MALDI-MS analysis.

Subsequently, in order to also identify the presence of the N-glycosylation site, the tryptic mixture of the sample was incubated with PNGase A and an aliquot of the mixture produced was again subjected to MALDI-MS analysis.

The study of the spectra obtained in the MALDI-MS analysis of the peptide mixtures of the two chains allowed to construct their "peptide map". The amino acid sequence of the two chains (light and heavy) was thus confirmed, covering 97% of the sequence of the light chain and 78.9% of the heavy chain. Partial cover of the sequence of the heavy chain is due to the fact that the region Δ[176-238] has no hydrolysis sites either for trypsin or for other specific enzymes or chemical agents. For both chains the correct removal of the signal peptide and the partial cyclization of the Gln residue in N-terminal position was found. It was also possible to identify Asn325 as a site of N-glycosylation.

With regard to the study of glycoforms, after incubation with PNGase A, the oligosaccharides were separated from the peptide component by Sep-Pak chromatography, concentrated and then analyzed in MALDI-MS. This analysis allowed to detect the presence of a series of signals attributable to the glycoforms present (FIG. 10). The glycosylation profile was the expected one for proteins expressed in plants, that is, of the paucimannose type with a fucosylated core with or without a xylose residue.

Example 9: Pharmacological Tests In Vitro Concerning Antigen Binding, Competition and Co-Localization of the Antigen/Antibody Bond The RTX PBS fraction (Example 7) was used in cytofluorimetry experiments to evaluate its binding activity to the CD20 antigen compared to commercial RituxiMab (Rituxan®).

For the cytofluorimetric analysis (FACS), MEC-1 cells were used; MEC-1 corresponds to a human cell line of B-cell chronic lymphocytic leukemia (B-CLL), able to express CD20, that is the epitope recognized by Rituximab. The first phase of the experiment consisted in screening the MEC-1 cells on which to determine the antibody bond in order to operate only on live B lymphocytes in the absence of cellular aggregates and debris due to apoptosis. The intensity of fluorescence (FLH-1) in the presence of Rituxan® and the analogous recombinant purified from rice seed (RTX PBS) was analyzed on the population of cells thus separated and collected (highlighted by the polygon in FIG. 11a, section A); in particular, 500,000 MEC-1 cells were incubated for 1 h at 37° C. with 5 ng/μL of Rituxan® or with the same amount of RTX PBS. FACS analysis occurred after incubation with the secondary antibody FITC-anti-human IgG. With this analysis it was possible to demonstrate that Rituxan® recognizes 98.91% (FIG. 11a, section B) of MEC-1 cells while RTX PBS recognizes 98.33% (FIG. 11a, section C). The dotted line in FIG. 11a, sections B and C represents the fluorescence contribution provided by the unrelated secondary antibody. This data, together with the mean fluorescence intensity (FIG. 11b), indicates that the two antibodies have the same ability to bind the CD20 antigen. The RTX PBS antibody confirmed that it recognizes CD20 even after direct marking with fluorescein, so much so that 99.15% of MEC-1 cells were positive.

In order to identify the location of the antigen-antibody bond, an immunofluorescence analysis was conducted under the microscope on the same cells analyzed by FACS; the MEC-1 cells were adhered on a slide and marked with DAPI (Sigma, 1 μg/μL) to display the nuclei and FastDil (Invitrogen, 1 μg/μL) to display the cell membranes. The Rituxan® and RTX PBS antibodies were instead shown by FITC anti-human IgG secondary antibody or, in the case of the RTX PBS antibody alone, by direct conjugation with the FITC molecule (fluoroscein-5-isothiocyanate). As is known in literature, CD20 is a 4-domain trans-membrane molecule present on the whole cell surface; however, after bonding with RituxiMab it tends to concentrate inside cholesterol-rich lipid structures known as lipid rafts. This characteristic allows the Rituximab molecules to position themselves in a restricted zone of the cell surface, bringing the Fc portions closer together so as to be able to bind the C1q factor and activate the complementary cascade or induce apoptosis. From the immunofluorescence analysis it was possible to confirm the concentration of the CD20 antigen in a single membrane region thanks to the co-localization of the signal given by the fluoresceinate antibody with that of FastDil; this evidence was even more clearly visible using RTX PBS conjugated directly with FITC.

For the competition assay (FIG. 12), MEC-1 cells were incubated for 10 min in a volume of 25 μL of Rituxan® (100 μg/mL) or a control antibody (anti-CD52, Campath-1 100 μg/mL). Then, 25 μL of FITC-labeled RTX antibody was added at a concentration of 10 μg/mL. After incubation for 1 h at 37° C. and elimination by washing of the unbound antibody fraction, the cells were subjected to cytofluorimetric analysis. In the competition assay, if the epitope recognized by Rituxan® or Campath-1 is the same as RTX PBS, a reduction of the bonding of RTX PBS to the antigen is expected, because the sites involved are already occupied. Therefore, as indicators of competition, cells with low fluorescence (between 10° and $10^2$) should be considered. Cells that showed low fluorescence in the presence of marked RTX PBS (and absence of other antibodies) were a mere 7.18% (FIG. 12A). On the contrary, in the competition assay with Rituxan®, more than 97% of cells showed low fluorescence intensity (FIG. 12C), indicating that Rituxan® and RTX PBS compete for the same site. In the presence of Campath, only 10.36% of the cells came within the field of low fluorescence (FIG. 12B), proving that RTX PBS and Campath recognize different epitopes.

It is clear that modifications and/or additions of parts can be made to the method for the stable production of a plant protein, in particular a whole recombinant antibody in a cereal endosperm as described heretofore, without departing from the field and scope of the present invention.

It is also clear that, although the present invention has been described with reference to some specific examples, a person skilled in the art shall certainly be able to achieve many other equivalent forms of method for the stable production of a plant protein, in particular a whole recombinant antibody in a cereal endosperm, having the characteristics as set forth in the claims and hence all coming within the field of protection defined thereby.

The invention claimed is:

1. An expression vector for the stable production of a whole recombinant antibody in a cereal endosperm, wherein said expression vector is a single vector comprising:
   an expression cassette for the light polypeptide chain (L) of the antibody,
   an expression cassette for the heavy polypeptide chain (H) of the antibody,
   wherein said expression cassette for the light polypeptide chain (L) and the expression cassette for the heavy polypeptide chain (H):
   a) are operatively linked inside a DNA segment that is inserted integrally into the genome of a plant;
   b) are each provided with the following regulatory elements of gene expression:
   i) an endosperm-specific promoter of natural or artificial origin,
   ii) a 5'-UTR comprising the nucleotide sequence of SEQ ID NO: 3;
   iii) a signal peptide of natural or artificial origin to target the recombinant polypeptide chain inside the lumen of the endoplasmic reticulum of the cells that make up the endosperm,
   iv) a 3'-UTR of natural or artificial origin,
   wherein the regulatory elements of gene expression i), ii), iii) and v) are identical between said expression cassettes of the light polypeptide chain (L) and the heavy polypeptide chain (H).

2. The expression vector of claim 1, wherein said cereal is rice.

3. The expression vector of claim 2, wherein said endosperm-specific promoter of natural or artificial origin is the promoter of the gene for rice glutelin 4 (GluB-4) comprising the nucleotide sequence of SEQ ID NO: 2.

4. The expression vector of claim 2, wherein the nucleotide sequence encoding the signal peptide comprises the nucleotide sequence of SEQ ID NO: 4.

5. The expression vector of claim 2, wherein said 3'-UTR is the NOS terminator comprising the sequence of SEQ ID NO: 7, or the terminator of the rice GluB-4 gene.

6. The expression vector of claim 2, wherein the nucleotide sequences encoding the mature form of the light polypeptide chain (L) of the antibody Rituximab or heavy polypeptide chain (H) of the antibody Rituximab comprise the nucleotide sequences of SEQ ID NO: 5 and SEQ ID NO: 6, respectively.

7. The expression vector of claim 1, wherein said vector further comprises an expression cassette encoding a selectable marker that functions in plants.

8. The expression vector of claim 1, wherein the sequences encoding the light polypeptide chain (L) and heavy polypeptide chain (H) of the antibody are optimized for expression in cereals through the use of preferential species-specific synonymous codons.

9. The expression vector of claim 1, wherein said vector comprises an expression cassette for selection of transformed cereal cells comprising:
   a constitutive promoter of natural or artificial origin,
   a sequence coding for the selectable marker in its natural or artificial synonymous version, and
   a terminator of natural or artificial origin suitable for a plant expression system.

10. The expression vector of claim 1, wherein said single expression vector has the sequence indicated in SEQ ID NO: 1.

11. A bacterial strain comprising the expression vector of claim 1.

12. A binary system for *Agrobacterium* spp. mediated transformation consisting of the expression vector of claim 1 and a complementary vector bearing the Vir region.

13. An organism selected from cereal plant cells, cereal plants and cereal plant seed, the organism being transformed by the expression vector of claim 1.

14. A method for the stable production of a whole recombinant antibody in a cereal endosperm, said method comprising:
   industrial processing of the transformed cereal plant seed of claim 13, and
   extraction and purification of the antibody.

15. The method of claim 14, wherein the yield of whole recombinant antibody stably produced is more than 0.6 grams of antibody per kilogram of endosperm.

* * * * *